United States Patent
Lee et al.

(10) Patent No.: US 9,902,935 B2
(45) Date of Patent: Feb. 27, 2018

(54) METHOD FOR GENERATION OF REGULATORY T-CELLS USING FACTORS SECRETED BY INKT CELLS

(71) Applicant: UNIVERSITY OF FLORIDA RESEARCH FOUNDATION, Gainesville, FL (US)

(72) Inventors: Hyeong Woo Lee, Gainesville, FL (US); Brian Samuel Wilson, Gainesville, FL (US)

(73) Assignee: UNIVERITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 278 days.

(21) Appl. No.: 14/763,002

(22) PCT Filed: Jan. 24, 2014

(86) PCT No.: PCT/US2014/012882
§ 371 (c)(1),
(2) Date: Jul. 23, 2015

(87) PCT Pub. No.: WO2014/116908
PCT Pub. Date: Jul. 31, 2014

(65) Prior Publication Data
US 2015/0361397 A1 Dec. 17, 2015

Related U.S. Application Data

(60) Provisional application No. 61/756,097, filed on Jan. 24, 2013.

(51) Int. Cl.
| | |
|---|---|
| C12N 5/071 | (2010.01) |
| C12N 5/00 | (2006.01) |
| C12N 5/02 | (2006.01) |
| A01N 63/00 | (2006.01) |
| C12N 5/0783 | (2010.01) |
| C12N 5/0784 | (2010.01) |
| A61K 35/17 | (2015.01) |
| A61K 35/12 | (2015.01) |

(52) U.S. Cl.
CPC ............ *C12N 5/0637* (2013.01); *A61K 35/17* (2013.01); *C12N 5/064* (2013.01); *A61K 2035/122* (2013.01)

(58) Field of Classification Search
None
See application file for complete search history.

(56) References Cited

U.S. PATENT DOCUMENTS

| | | | |
|---|---|---|---|
| 2006/0115899 A1 | 6/2006 | Buckner et al. | |
| 2007/0184031 A1* | 8/2007 | Prabhakar | A61K 39/0008 424/93.7 |
| 2008/0175830 A1* | 7/2008 | Steinman | C12N 5/0636 424/93.71 |
| 2010/0041145 A1 | 2/2010 | Gregori et al. | |

FOREIGN PATENT DOCUMENTS

WO    WO 2008/024242    2/2008

OTHER PUBLICATIONS

Boks, M.A. et al. "IL-10-generated tolerogenic dendritic cells are optimal for functional regulatory T cell induction—A comparative study of human clinical-applicable DC" *Clinical Immunology*, 2012, vol. 142, No. 3, pp. 332-342.
Fantini, M.G. et al. "In vitro generation of CD4+CD25+ regulatory cells from murine naive T cells" *Nature Protocols*, 2007, vol. 2, No. 7, pp. 1789-1794.
Fu, S. et al. "TGF-β Induces Foxp3 + T-Regulatory Cells from CD4 + CD25—Precursors" *American Journal of Transplantation*, 2004, vol. 4, No. 10, pp. 1614-1627.
NCBI Reference Sequence No. NP_002955.2, Dec. 9, 2012, pp. 1-4.
Porcelli, S. et al. "Analysis of T Cell Antigen Receptor (TCR) Expression by Human Peripheral Blood CD4'8' α/β T Cells Demonstrates Preferential Use of Several Vβ Genes and an Invariant TCRα chain" *J. Exp. Med.*, Jul. 1993, vol. 178, pp. 1-16.
Naidenko, O.V. et al. "Binding and Antigen Presentation of Ceramide-containing Glycolipids by Soluble Mouse and Human CD1d Molecules" *J. Exp. Med.*, Oct. 18, 1999, vol. 190, No. 8, pp. 1069-1079.
Wilson, S.B. et al. "Multiple differences in gene expression in regulatory Vα24JαQ T cells from identical twins discordant for type I diabetes" *Proc. Natl. Acad. Sci. U.S.A.*, Jun. 20, 2000, vol. 97, No. 13, pp. 7411-7416.
Moodycliffe, A.M. et al. "Immune suppression and skin cancer development: regulation by NKT cells" *Nat. Immunol.*, Dec. 2000, vol. 1, No. 6, pp. 521-525.
Naumov, Y.N. et al. "Activation of CD1d-restricted T cells protects NOD mice from developing diabetes by regulating dendritic cell subsets" *Proc. Natl. Acad. Sci. U.S.A.*, Nov. 20, 2001, vol. 98, No. 24, pp. 13838-13843.

(Continued)

Primary Examiner — Amy E Juedes
(74) Attorney, Agent, or Firm — Saliwanchik, Lloyd & Eisenschenk

(57) ABSTRACT

The current invention concerns the use of PIP or S100A8 for the generation of regulatory T cells. The current invention provides a method of generating regulatory T cells by contacting immature DC with PIP or S100A8 to produce tolerogenic DC and further contacting naïve T cells to the tolerogenic DC to produce regulatory T cells. The invention also concerns PIP protein where immature DC contacted with PIP produce tolerogenic DC that induce conversion of naïve T-cells into regulatory T cells. The invention also concerns S100A8 protein where immature DC contacted with S100A8 produce tolerogenic DC that induce conversion of naïve T-cells into regulatory T cells. The invention also provides methods for identification of factors secreted by iNKT cells that induce conversion of immature DC into tolerogenic DC. The subject invention also concerns using regulatory T cells for treatment and/or management of cancer or the diseases of the immune system.

11 Claims, 25 Drawing Sheets

(56) References Cited

OTHER PUBLICATIONS

Sharif, S. et al. "Activation of natural killer T cells by α-galactosylceramide treatment prevents the onset and recurrence of autoimmune Type 1 diabetes" *Nat. Med.*, 2001, vol. 7, pp. 1057-1062.

Wilson, S.B. et al. "Extreme Th1 bias of invariant Vα24JαQ T cells in type 1 diabetes" *Nature*, 1998, vol. 391, pp. 177-181.

Behar, S.M. et al. "Susceptibility of Mice Deficient in CD1D or TAP1 to Infection with *Mycobacterium tuberculosis*" *J. Exp. Med.*, Jun. 21, 1999, vol. 189, No. 12, pp. 1973-1980.

Kakimi, K. et al. "Natural Killer T Cell Activation Inhibits Hepatitis B Virus Replication In Vivo" *J. Exp. Med.*, Oct. 2, 2000, vol. 192, No. 7, pp. 921-930.

Gonzalez-Aseguinolaza, G. et al. "α-Galactosylceramide-activated Vα14 natural killer T cells mediate protection against murine malaria" *Proc. Natl. Acad. Sci. U.S.A.*, Jul. 18, 2000, vol. 97, No. 15, pp. 8461-8466.

Hegde, S. et al. "NKT cells direct monocytes into a DC differentiation pathway" *J. Leuko. Biol.*, May 2007, vol. 81, pp. 1224-1235.

Hori, S. et al. "Control of Regulatory T Cell Development by the Transcription Factor Foxp3" *Science*, Feb. 14, 2003, vol. 299, pp. 1057-1061.

Vogl, T. et al. "Mrp8 and Mrp14 are endogenous activators of Toll-like receptor 4, promoting lethal, endotoxin-induced shock" *Nat. Med.*, Sep. 2007, vol. 13, No. 9, pp. 1042-1049.

Exley, M.A. et al. "Selective activation, expansion, and monitoring of human iNKT cells with a monoclonal antibody specific for the TCR α-chain CDR3 loop" *Eur. J. Immunol.*, 2008, vol. 38, pp. 1756-1766.

Hou, R. et al. "Interleukin-12 and interleukin-2-induced invariant natural killer T-cell cytokine secretion and perforin expression independent of T-cell receptor activation" *Immunol.*, 2003, vol. 110, pp. 30-37.

Ferret-Bernard, S. et al. "Proteomic profiling reveals that Th2 inducing dendritic cells stimulated with helminth antigens have a 'limited maturation' phenotype" *Proteomics*, 2008, vol. 8, pp. 980-993.

Vincent, M.S. et at. "CD1-dependent dendritic cell instruction" *Nat. Immunol.*, Dec. 2002, vol. 3, No. 12, pp. 1163-1168.

Wilson, S.B. et al. "Janus-like role of regulatory iNKT cells in autoimmune disease and tumour immunity" *Nat. Rev. Immunol.*, Mar. 2003, vol. 3, pp. 211-222.

Hegde, S. et al. "Autoreactive natural killer T cells: promoting immune protection and immune tolerance through varied interactions with myeloid antigen-presenting cells" *Immunol.*, 2010, vol. 130, pp. 471-483.

Mars, L.T. et al. "Invariant NKT cells inhibit development of the $Th_{17}$ lineage" *Proc. Natl. Acad. Sci. U.S.A.*, Apr. 14, 2009, vol. 106, No. 15, pp. 6238-6243.

Hayflick, J.S. et al. "The Intercellular Adhesion Molecule (ICAM) Family of Proteins" *Immunol. Res.*, 1998, vol. 17, pp. 313-327.

Takahashi, T. et al. "Analysis of Human Vα24$^+$CD4$^+$NKT Cells Activated by α-Glycosylceramide-Pulsed Monocyte-Derived Dendritic Cells" *J. Immunol.*, 2000, vol. 164, pp. 4458-4464.

Boyd, J.H. et al. "S100A8 and S100A9 Mediate Endotoxin-Induced Cardiomyocyte Dysfunction via the Receptor for Advanced Glycation End Products" *Circ. Res.*, 2008, vol. 102, pp. 1239-1246.

Caielli, S. et al. "On/Off TLR Signaling Decides Proinflammatory of Tolerogenic Dendritic Cell Maturation upon CD1d-Mediated Interaction with Invariant NKT Cells" *J. Immunol.*, 2010, vol. 185, pp. 7317-7329.

Chen, X. et al. "Phosphatidylserine Regulates the Maturation of Human Dendritic Cells" *J. Immunol.*, 2004, vol. 173, pp. 2985-2994.

Hermans, I.F. et al. "Dendritic Cell Function Can Be Modulated through Cooperative Actions of TLR Ligands and Invariant NKT Cells" *J. Immunol.*, 2007, vol. 178, pp. 2721-2729.

Steinman, R.M. et al. "Avoiding horror autotoxicus: The importance of dendritic cells in peripheral T cell tolerance" *Proc. Natl. Acad. Sci. U.S.A.*, Jan. 8, 2002, vol. 99, No. 1, pp. 351-358.

Jonuleit, H. et al. "Induction of Interleukin 10-producing, Nonproliferating CD4$^+$T Cells with Regulatory Properties by Repetitive Stimulation with Allogeneic Immature Human Dendritic Cells" *J. Exp. Med.*, Nov. 6, 2000, vol. 192, No. 9, pp. 1213-1222.

Albert, M.L. et al. "Dendritic cell maturation is required for the cross-tolerization of CD8+ T cells" *Nat. Immunol.*, Nov. 2001, vol. 2, No. 11, pp. 1010-1017.

Tang, Q. et al. "Visualizing regulatory T cell control of autoimmune responses in nonobese diabetic mice" *Nat. Immunol.*, Jan. 2006, vol. 7, No. 1, pp. 83-92.

Banchereau, J. et al. "Immunobiology of Dendritic Cells" *Annu. Rev. Immunol.*, 2000, vol. 18, pp. 767-811.

Rissoan, M.C. "Reciprocal Control of T Helper Cell and Dendritic Cell Differentiation" *Science*, Feb. 19, 1999, vol. 283, pp. 1183-1186.

Liu, Y.J. et al. "Dendritic cell lineage, plasticity and cross-regulation" *Nat. Immunol.*, Jul. 2001, vol. 2, No. 7, pp. 585-589.

Kitamura, H. et al. "The Natural Killer T (NKT) Cell Ligand α-Galactosylceramide Demonstrates Its Immunopotentiating Effect by Inducing Interleukin (IL)-12 Production by Dendritic Cells and IL-12 Receptor Expression on NKT Cells" *J. Exp. Med.*, Apr. 5, 1999, vol. 189, No. 7, pp. 1121-1128.

Contasta, I. et al. "Relationships Between the Activity of MMP1/TIMP1 Enzymes and the TH1/TH2 Cytokine Network" *Cancer Biother. Radiopharm.*, 1999, vol. 14, No. 6, pp. 465-475.

\* cited by examiner

METHOD FOR GENERATION OF REGULATORY T-CELLS USING FACTORS SECRETED BY INKT CELLS

CROSS-REFERENCE TO RELATED APPLICATIONS

This application is the U.S. national stage application of International Patent Application No. PCT/US2014/012882, filed Jan. 24, 2014, which claims the benefit of U.S. Provisional Application Ser. No. 61/756,097, filed Jan. 24, 2013, the disclosures of both of which are hereby incorporated by reference in their entirety, including all figures, tables and amino acid or nucleic acid sequences.

This invention was made with government support under the contract numbers 2RO1 AI 4505-06AI and U19 AI046130 awarded by the US National Institutes of Health; and with support under the contract number 1-2004-771 awarded by JDRF. The government has certain rights in the invention.

BACKGROUND OF THE INVENTION

Human invariant Natural Killer T (iNKT) cells are a group of T cells that have a restricted usage of invariant Vα24-Jα18 T-cell receptor (TCR) and express several cell surface proteins found on Natural killer (NK) cells (Porcelli et al., 1993). iNKT cells share functional and phenotypic homology with both Natural Killer (NK) cells and T cells (FIG. 16). iNKT cells are restricted by the non-polymorphic class Ib molecule CD1d through presentation of glycolipid antigen (Naidenko et al., 1999), resulting in burst secretion of several cytokines, in particular IL-4 and INF-γ (Wilson et al., 2000). The rapid secretion of cytokines implies that iNKT cell may play an important role in modulating the upcoming immune responses and immunopathology. They regulate tumor immunity (Moodycliffe et al., 2000), diabetes (Naumov et al., 2001; Sharif et al., 2001; Wilson et al., 1998), and protection against bacteria (Behar et al., 1999), virus (Kakimi et al., 2000), and parasitic infections (Gonzalez-Aseguinolaza et al., 2000).

iNKT cells have been shown to promote peripheral tolerance in a number of model systems, but their regulatory effects remains poorly understood. Hegde et al. showed that soluble factors secreted by human iNKT cells instruct human peripheral blood monocytes to differentiate into myeloid APCs that have suppressive properties. Additionally, human iNKT cells direct primary human peripheral blood monocytes to differentiate into cells resembling immature myeloid Dendritic Cells (DC) (Hedge et al., 2007). iNKT cell activation by recognition of CD1d expressed on monocytes resulted in secretion of GM-CSF and IL-13 which promoted monocyte differentiation. The resulting myeloid cells showed up-regulation of DC-SIGN, little or no expression of CD14, and moderate expression of co-stimulatory markers, CD40 and CD86, and thus had a cell surface phenotype consistent with that of immature myeloid DC. Furthermore they revealed localization of MHC class II molecules in LAMP-1$^+$ intracellular vesicles as is characteristic of immature myeloid DC. When exposed to lipopolysaccharide (LPS), immature myeloid DC underwent changes associated with DC maturation, including up-regulation of CD83 and CCR7, and relocation of MHC class II molecules to the cell surface (Hedge et al., 2007). Importantly, DC fails to mature normally in both human and rodent autoimmune diabetes. Furthermore, transfer of highly mature DC protects NOD mice from disease. Therefore, defects in antigen presenting cells and CD1d-restricted T cells may cause the development of pathogenic autoimmune T cells and type 1 diabetes. It is believed that disease progression is influenced by a fine-balance where a $T_H1$-like response is critical for β cell destruction and movement towards overt disease; whereas, if the autoimmune T cell pool becomes biased towards $T_H2$-like cells (e.g., that can inhibit $T_H1$ cells via IL-4 or IL-10), either naturally or by activation or transfer of the appropriate CD1d-restricted T cell subset, the disease process may be halted.

DC is a key mediator of adaptive immunity. In the absence of infection, DC in peripheral tissues is resting in an immature state with limited ability to stimulate naïve T cells. However, after infection, DC undergo maturation, a process characterized by phenotypic changes resulting in improved ability to promote T cell responses. DC maturation can be induced by direct stimulation through DC expressed TLRs, or indirectly by exposure to cytokines released by local immune or nonimmune cells stimulated via their own TLRs. iNKT cells can promote enhanced T cell responses when activated by a powerful stimulus such as the synthetic glycolipid, α-Galactosylceramide (α-GalCer), implying that they can provide all of the signals required for DC activation (Hermans et al., 2007). The mechanisms controlling the generation of a proinflammatory DC as opposed to tolerogenic DC is critical in the development and progression of autoimmune diseases.

Steinman and co-workers have proposed that in the absence of infection or inflammation, there is a steady state flux of immature DC that capture and process endogenous antigens (Steinman et al., 2002). These DC then define immunologic self-tolerance by way of specifically silencing autoreactive T cells and promoting the development of regulatory T cells (Jonuleit et al., 2000). While immature DC appear to harbor the ability to tolerate self and foreign antigens, there are many recent examples of DC differentiated both in vivo and in vitro with potent tolerogenic capacity (Hedge et al., 2007; Albert et al., 2001). Importantly, the Bluestone group recently demonstrated that in vivo, regulatory T cells ($T_{reg}$) directly interacted with dendritic cells bearing islet antigen and that this preceded the inhibition of T helper cell activation by DC (Tang et al., 2006). The explanation for these apparently contradictory functions appears to lie in the remarkable capacity of immature dendritic cells to differentiate into specific functional subtypes during maturation (Banchereau et al., 2000). Depending on the lineage (i.e. myeloid or lymphoid) and maturation stimulus, DC potently control T cell effector function and cytokine profiles (Rissoan et al., 1999; Liu et al., 2001). The exchange of information between DC and T cells is not unilateral. While DC are required for the efficient priming of antigen-specific lymphocyte responses, T cells in turn are also required for optimal DC maturation (Rissoan et al., 1999). Several investigations, including our own, have underscored the regulatory importance of DC/iNKT cell cross talk in shaping the immune response and controlling the relative percentage of DC subsets (Hedge et al., 2007; Kitamura et al., 1999). Autoreactive iNKT cells have also recently been shown directly to potently induce DC maturation, and mature DC that had been exposed to iNKT cells produced more IL-10 than IL-12, a phenotype consistent with a tolerogenic function (Vincent et al., 2002).

BRIEF SUMMARY OF THE INVENTION

The current invention concerns the use of prolactin induced protein (PIP) or S100 calcium binding protein A8

(S100A8) for the generation of $T_{reg}$. An aspect of the current invention provides a method of generating $T_{reg}$ by contacting immature DC with PIP or S100A8 to produce tolerogenic DC and further contacting tolerogenic DC with naïve T cells to induce the conversion of naïve T cells to $T_{reg}$.

Thus, one aspect of the invention provides for the use of PIP in the generation of tolerogenic DC which can, then, be used to produce naïve $T_{reg}$ from naïve T-cells into $T_{reg}$.

Another aspect of the invention provides for the contacting of immature DC with S100A8 to produce tolerogenic DC that induce conversion of naïve T-cells into $T_{reg}$.

Yet another aspect of the invention provides methods for identification of factors secreted by iNKT cells that induce conversion of immature DC into tolerogenic DC.

The subject invention also provides methods of using $T_{reg}$ for treatment or management of diseases, specifically, cancer and diseases of the immune system, more specifically, inflammatory or auto-immune diseases.

BRIEF DESCRIPTION OF THE SEQUENCES

Figure 1:
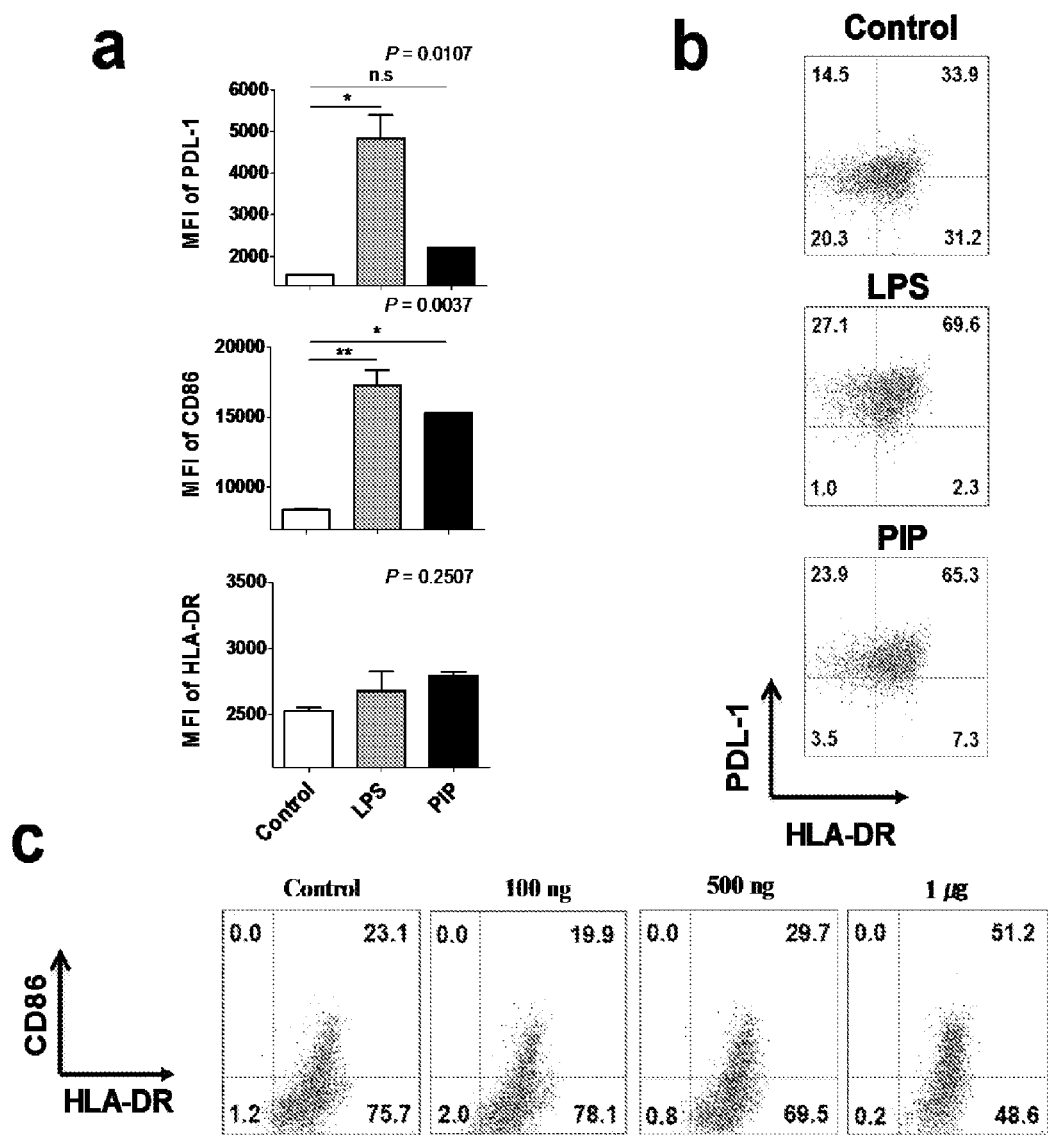
FIGS. 1A-C. Effect of Prolactin induced protein (PIP) on DC maturation. (a) Expression of HLA-DR, CD86, and PDL-1 on the surface of matured DC by LPS and PIP. (b) FACS profile of mature DC. (c) Effect of PIP on Dendritic maturation in a dose dependent manner. The maturation of immature DC was assessed by estimating the expression levels of PDL-1, CD86, and HLA-DR on the DC surface by FACS. *$P<0.05$; **$P<0.001$. Results are representative of three independent experiments. Error bars indicate mean±s.d.

```
SEQ ID NO: 1: (human S100A8):
MLTELEKALNSIIDVYHKYSLIKGNFHAVYRDDLKKLLETECPQYIRKKG

ADVWFKELDINTDGAVNFQEFLILVIKMGVAAHKKSHEESHKE.

SEQ ID NO: 2: (human prolactin inducible protein
(PIP); signal peptide underlined):
MRLLQLLFRASPATLLLVLCLQLGANKAQDNTRKIIIKNFDIPKSVRPND

EVTAVLAVQTELKECMVVKTYLISSIPLQGAFNYKYTACLCDDNPKTFYW

DFYTNRTVQIAAVVDVIRELGICPDDAAVIPIKNNRFYTIEILKVE.

SEQ ID NO: 3: (mature human PIP):
QDNTRKIIIKNFDIPKSVRPNDEVTAVLAVQTELKECMVVKTYLISSIPL

QGAFNYKYTACLCDDNPKTFYWDFYTNRTVQIAAVVDVIRELGICPDDAA

VIPIKNNRFYTIEILKVE.
```

DETAILED DISCLOSURE OF THE INVENTION

A first aspect of the invention provides methods for the production of $T_{reg}$ cells from naïve T-cells using tolerogenic DC produced factors secreted by iNKT cells that induce maturation of immature DC into tolerogenic DC. $T_{reg}$ are a subset of T cells that have immunosuppressive properties. These cells were formerly known as suppressor T cells. Due to their immunosuppressive characteristics, $T_{reg}$ play a role, among other things, in maintaining tolerance to self-antigens and can be used to abrogate or ameliorate autoimmune diseases. Thus, $T_{reg}$ are useful in treatment and management of diseases, for example, autoimmune diseases and cancer and may also be used to facilitate organ transplant.

Naïve T cells are a subset of T-cells that have undergone differentiation in the bone marrow after positive and negative central selection processes in the thymus; however, naïve T cells have not been exposed to cognate antigen. Naïve T cells may also be referred to as $T_H0$ cells.

Immature DC are precursors of mature DC and are characterized by high endocytic activity and lower ability to activate T cells. Immature DC are actively involved in endocytosing foreign particles, such as bacteria and viruses, as well as self antigens, such as membranes from the cells of a subject, in search of a presentable antigens. Once an immature DC encounters a presentable antigen it is converted into a mature DC.

Tolerogenic DC belong to a subset of mature DC that have immunosuppressive properties. One of the mechanisms through which tolerogenic DC exert their immunosuppressive effects is by inducing generation of $T_{reg}$ from naïve T cells.

Thus, one aspect of the subject invention provides methods for generating $T_{reg}$. Accordingly, of prolactin induced protein (PIP) or S100 calcium binding protein A8 (S100A8) can be used to generate $T_{reg}$ from naïve T cells. In this aspect of the invention $T_{reg}$ are produced by contacting immature DC with compositions comprising PIP and/or S100A8 to produce tolerogenic DC and further contacting the tolerogenic DC with naïve T cells to produce $T_{reg}$. $T_{reg}$ cells produced by the current invention are CD4+CD25+Foxp3+ T cells. For the purposes of this application, mature PIP (polypeptides lacking the leader sequence (amino acids 1-28 of SEQ ID NO: 2) or PIP polypeptides including the leader sequences can be used for the generation of $T_{reg}$. The sequences of PIP and S100A8 are known in the art and can be obtained from public databases, such as the Protein Knowledgebase (UniprotKB). Information, including sequence information for S100A8 can be accessed at www.uniprot.org/uniprot/P05109 (last modified Oct. 3, 2012, Version 139). Information, including sequence information, for PIP can be accessed at www.uniprot.org/uniprot/P12273 (last modified Oct. 3, 2012, Version 119). The accession numbers for S100A8 and PIP in the Protein Knowledgebase (UniprotKB) are P05109 and P12273, respectively.

Another aspect of the invention provides methods for the treatment and management/modulation of diseases, for example cancer or the diseases of the immune system, such as, autoimmune diseases and inflammatory diseases. The autoimmune diseases which may be treated by the $T_{reg}$ of the current invention include, but are not limited to, Addison's disease, autoimmune hepatitis, autoimmune hyperlipidemia, autoimmune myocarditis, autoimmune pancreatitis, autoimmune retinopathy, axonal and neuronal neuropathies, cardiomyopathy, Crohn's disease, insulin dependent diabetes (Type 1 diabetes), juvenile diabetes, multiple sclerosis (MS), systemic lupus erythematosus (SLE), Lyme disease, palindromic rheumatism, psoriasis, psoriatic arthritis, rheumatic fever, rheumatoid arthritis. The inflammatory diseases which may be treated by the $T_{reg}$ of the current invention include, but are not limited to, inflammation of skin, eye, liver, gastro-intestinal, kidney, cardio-vascular system, respiratory tract, endocrine, joint, musculoskeletal system, peripheral nervous system, central nervous system, and lung.

Another aspect of the invention provides methods for identification of novel factors secreted by iNKT cells that induce conversion of immature DC into tolerogenic DC. In this aspect of the invention, In this aspect of the invention, CD4+CD25−Foxp3− T cells are contacted with cell culture supernatant from CD4+ iNKT cells that have been activated by anti-CD3 antibody (either plate-bound anti-CD3 antibody, anti-CD3 antibody bound to a solid support (e.g., beads, etc.). In certain embodiments of this aspect of the invention, cell culture supernatant from the anti-CD3 stimulated CD4+ iNKT can be collected after about 5 days of incubation (measured from the time the anti-CD3 antibody is added to the CD4+ iNKT cell culture) and, optionally, subjected to further purification. Further purification of the cell culture supernatant for the identification of the cell culture supernatant can comprise fractionation with FPLC using HiTrap DEAE FF, HiTrap CM FF, and HiTrap Blue column chromatography (GE Healthcare) using FPLC. Individual fractions obtained from the column chromatography step can be tested for the ability to cause upregulation of HLA-DR and CD86 on the surface of DC and further analyzed to determine or identify the compounds that activate DC. Certain additional embodiments of this aspect of the invention provide for comparing DC activation caused by compositions comprising PIP and/or S100A8 with compounds isolated according to this aspect of the invention.

Another aspect of the invention provides for a composition comprising PIP and/or S100A8 in combination with iNKT cells and/or $T_{reg}$ cells. Another aspect of the invention provides a composition comprising iNKT cells and/or $T_{reg}$ cells in combination with one or more of the proteins listed in Table 1.

Figure 15:
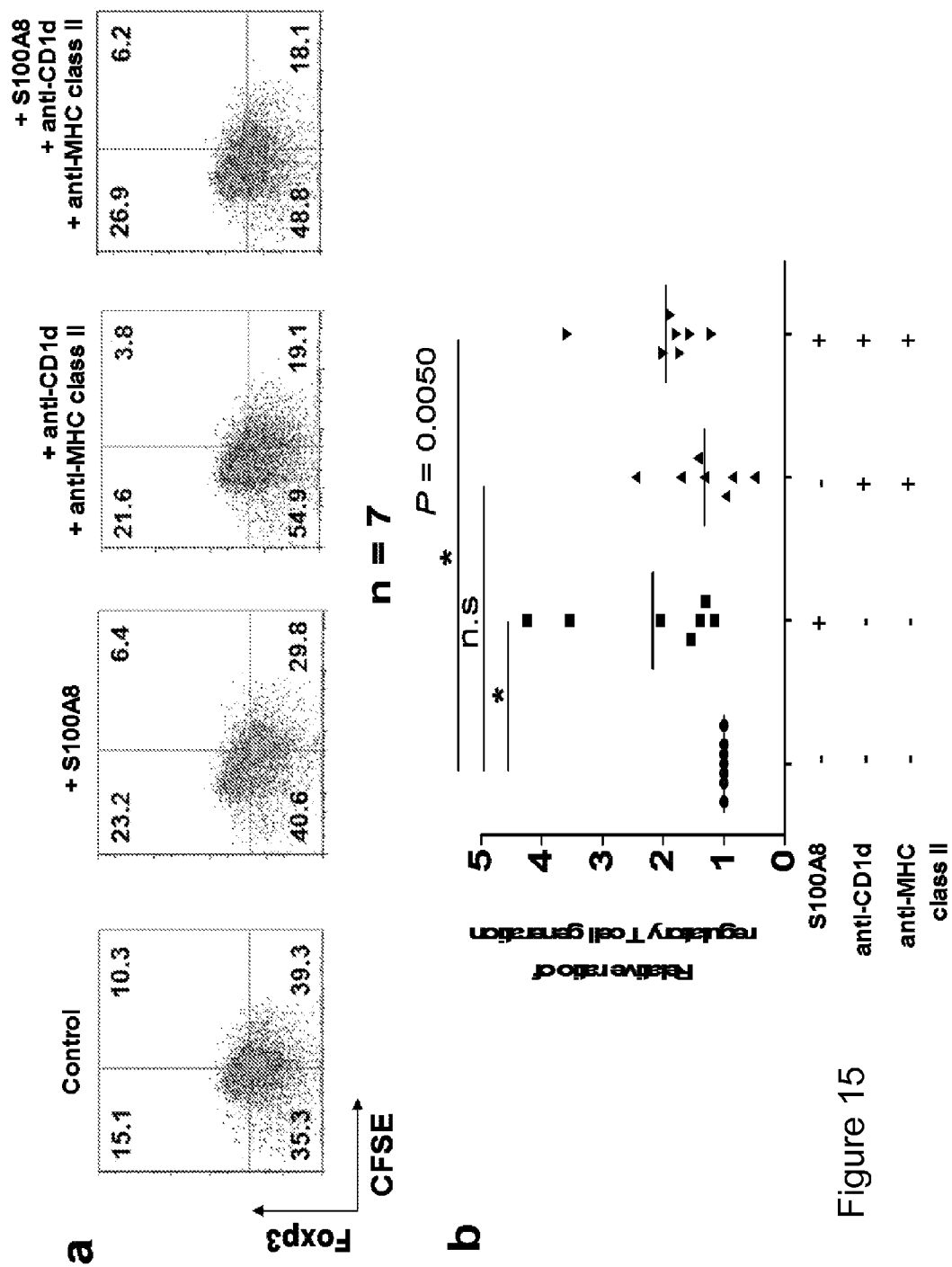
FIGS. 15A-B. S100A8 and combined plate-bound anti-CD1d/MHC class II antibody stimulated immature DC induce CD4+CD25+Foxp3+ T cells. Immature DC transferred to anti-CD1d/MHC class II antibody coated plate, and cultured 48 hours with or without soluble S100A8 to allow the induction of tolerogenic DC. Tolerogenic DC were co-cultured with CFSE labeled CD4+CD25-Foxp3- T cell with 1 μg/ml anti-CD3, 500 ng/ml anti-CD28, and 50 U/ml IL-2 for 5 days. Developments of $T_{reg}$ cells were assessed expression level of CD4, CD25, and Foxp3 by FACS analysis.
Figure 16:
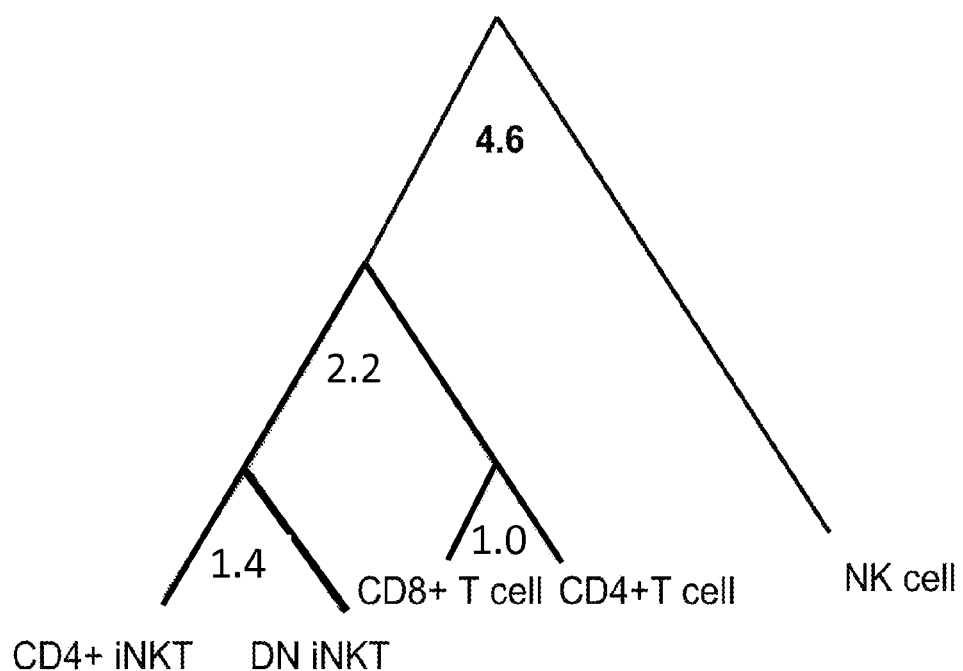
FIG. 16. Hierarchical clustering lineage analysis for 5 CD4+ and DN iNKT cell clones raised from normal donors, three alloreactive CD8+ T cell clones, 3 tetanus reactive CD4+ T cell clones and 16 NK cell clones.

S100A8 generated $T_{reg}$ in a concentration dependent manner (FIG. 24) and $T_{reg}$ generation was enhanced by adding the anti-CD1d and anti-MHC class II antibodies (FIG. 15). However, S100A8 was expressed both in CD4+ iNKT and DN iNKT cells, a finding in conflict with our hypothesis that CD4+ iNKT cells generate tolerogenic DC for differentiation of $T_{reg}$ from naïve T cells. It means that there are other candidates for the DC maturation factors which are expressed only in the CD4+ iNKT cells or other control mechanisms which reduce or inhibit S100A8 function in DN iNKT cells.

TABLE 1

The supernatants of CD4+ iNKT cells induced by anti-CD3 antibody were analyzed for their protein components by Mass spectrometry.

| Group | Protein |
| --- | --- |
| A* | S100A8 (s100 calcium-binding protein A8, MRP8) |
| B | Prolactin induced protein |
| C | ATP-binding cassette |
|  | Desmoplakin isoform 1 |
|  | Haptoglobin |
|  | Serpin peptidase inhibitor clade A, member 3 |
|  | (SERPINA3, ACT, a-1-antichymotrypsin) |
|  | Transferrin |
|  | Transthyretin |
| D | Ceruloplasmin |
|  | Hemopexin |
|  | Mesotrypsin |
|  | Orosomucoid 1 |
|  | Serine (or cysteine) proteinase inhibitor, clade B |

*Group A: The protein which hit 8 times among 9 sample analysis of 4 independent experiments.
Group B: The protein which hit 7 times among 9 sample analysis of 4 independent experiments.
Group C: The proteins which hit 6 times among 9 sample analysis of 4 independent experiments.
Group D: The proteins which hit 5 times among 9 sample analysis of 4 independent experiments.

S100A8 (SEQ ID NO: 1; encoded by Mrp8) belongs to the calcium-binding S100 protein family, and S100A8 forms $Ca^{2+}$ dependent heterodimer/heterotetramer complexes with S100A9, human S100A8 consists of 93 amino acids, contains two EF-hand motifs (aa 12-47 and 46-81) and one high-affinity Ca binding site (aa 59-70) and has a molecular weight of about 10 kDa. Prolactin induced protein (PIP) (also referred to as gross cystic disease fluid protein-15 (GCDFP-15) or prolactin inducible protein) binds to CD4 PIP (SEQ ID NO: 2) is a 17 kDa glycoprotein present in various human body fluids.

Additional aspects of the invention provide methods of treating cancer, modulating mucosal immunity and suppressing an allergic response. Thus, one aspect of the invention provides for inhibiting the expression of PIP in tumors or cancer cells of a subject in order to render the tumors or cancer cells more susceptible the effects of cytotoxic T lymphocytes. Another aspect of the invention provides for the modulation of mucosal immunity and suppression of the immune response comprising inhibition of PIP expression in mucosal tissues, submucosal glands of the bronchi and apocrine glands of the skin In either of these aspects of the invention, PIP expression can be inhibited by a number of mechanisms, including gene silencing with siRNA delivered according to methods known in the art or the use of antibodies that neutralize or inhibit PIP activity.

Additional aspects of the invention provide a method of modulating an autoimmune disease in a subject, said method comprising (a) obtaining a population of subject-compatible naïve T cells; (b) producing a Treg cell enriched composition from said population of cells by contacting the naïve T-cells with a composition comprising tolerogenic DC; and (c) introducing said induced and enriched Treg cell populations into said subject to modulate said autoimmune reaction in said subject. In certain embodiments, the population of naïve T-cells cells is obtained from said subject, obtained from a donor distinct from said subject, and/or harvested from peripheral blood or the subject or a donor distinct from the subject and contacted with tolerogenic DC produced by contacting immature DC with PIP or S100A8 to produce. In certain embodiments, the step of producing Treg cells comprises expanding Treg cells, and/or enriching or isolating Treg cells from the population of cells obtained in the production step. Expansion of Treg cells, in an ex vivo setting, can be performed according to methods known in the art. An Treg cell enriched composition is one in which the percentage of Treg cells is higher than the percentage of Treg cells in the originally obtained population of cells. In particular embodiments, Treg cells can be enriched by 50%, two to 10-fold, two to 20-fold, or 50-fold to 800-fold.

The terms "treat", "treating" or treatment" are intended to indicate that at least an amelioration of one or more symptoms associated with a disease in the subject is achieved, where amelioration is used in a broad sense to refer to at least a reduction in the magnitude of a parameter, e.g. symptom, associated with the condition being treated. The term "subject" is intended to include "mammals", such as dogs, cats, rodents (e.g., mice, guinea pigs, and rats), and primates (e.g., humans, chimpanzees, and monkeys). In certain embodiments, the subject will be a human. In various embodiments, the methods of treatment can include a step of diagnosing the presence of an autoimmune disease according to methods known in the art.

MATERIALS AND METHODS

Cell Lines

CD1d-restricted T cell clones were generated by single cell sorting using MoFlo (Becton Dickinson, Mountainview, Calif.). Briefly, NKT cells were sorted using the 6B11-fluorochrome conjugated antibody (an mAb specific for the invariant Vα24JαQ CDR3 loop) (Exley et al., 2008) and single-cell sorts were grown with a mixture of irradiated (5000 rads) allogenic peripheral blood mononuclear cells at 75,000 per well. The NKT clones were then frozen in liquid nitrogen until further use. When thawed, the clones were expanded using 100 ng/ml α-GalCer and Gammar irradiated peripheral blood mononuclear cells (PBMC).

Culture of iNKT Cell Clones iNKT cell clones were expanded by culturing in RPMI 1640 (BioWhitaker, Wakervillie, Md.) supplemented with 10% heat inactivated Fetal Bovine Serum (FBS, Atlanta biologicals, Norcross, Ga.), $25 \times 10^6$ irradiated PBMC, 100 ng/ml α-GalCer, 2 mM L-glutamine, 10 mM HEPES buffer, 100 U/ml penicillin (Biowhittaker), and 100 μg/ml streptomycin sulfate (Biowhittaker) (Hou et al., 2003).

The PBMC used as feeder cells for iNKT cells were isolated by Ficoll-Paque (Amersham Pharmarcia Biotech, Uppsala, Sweden) density gradient centrifugation from venous blood collected from health donors. Cells were incubated at 37° C. in a humidified chamber with 5% $CO_2$. After 18-24 hr, 50 U/ml human recombinant IL-2 (Roche, Mannheim, Germany) and 10 U/ml human IL-7 (Roche)

were added onto co-cultured the iNKT cells with the feeder cells. On day 5, half of the medium was changed with fresh medium supplemented with 50 U/ml IL-2 and 10 U/ml IL-7. During days 10-14, iNKT cells were split for further expansion (Steinman et al., 2002). Purity of expanded cells was checked by flow cytometry using CD4, CD8, and 6B11 fluorochrome-conjugated antibodies.

Cytokine Profiling

Clones were stimulated with anti-CD3 antibody as described above. Supernatant was taken 24 hours later and stored at −80° C. A commercial ELISA based assay system (RayBio Human Cytokine Antibody Array C series 1000) was used as described in www.raybiotech.com/manual/C_Series_1000.pdf. All samples were run in duplicate. Signals were arbitrarily scored as high, low or absent.

Reverse Transcription-Polymerase Chain Reaction Analysis

For reverse transcription polymerase chain reaction (RT-PCR), mRNA was isolated with RNeasy mini kit (Qiagen Co., Valencia, USA) according to manufacturer's instructions. For reverse transcription polymerase chain reaction (RT-PCR), mRNA was isolated with RNeasy mini kit (Qiagen Co., Valencia, USA) according to manufacturer's instructions. One μg of total RNA, S100A8-F (sense, ACC GAG CTG GAG AAA GCC TTG AAC TCT; SEQ ID NO: 4) and S100A8-R (antisense, CTC TTT GTG GCT TTC TTC ATG GCT TTT; (SEQ ID NO: 5) primers, and the reverse transcriptase Super Script II (Invitrogen Co., Carlsbad, Calif.) was used for the RT-PCR. The first strand of cDNA was made at 50° C. for 30 min, and 34 cycles (94° C. for 30 seconds, 55° C. for 30 seconds, 72° C. for 60 seconds) were used to amplify S100A8 gene, yielding a PCR product with an expected size of 273 base pair (bp).

Preparation of Anti-CD3 Activated NKT Cell Supernatant

To preparation of supernatant of CD4+ iNKT cell activated with anti-CD3 antibody, the plate treated with 100 ng/ml of anti-CD3 antibody (Ancell, Bayport, Minn.) incubated at 4° C. overnight. After washing with three times the plates with 10% FBS RPMI 1640 medium, CD4+ iNKT cells were added and cultured in 5% $CO_2$ incubator at 37° C. After 7 days, supernatants were collected and filtered with 0.22 μm filter for remove cell debris, etc.

Purification of DC Maturation Factors with FPLC

To purify the DC maturation factors, we applied protein samples into AKTA Explorer 100 FPLC instrument (GE healthcare, Piscataway, N.J.). Briefly, 30 ml anti-CD3 antibody activated supernatant of NKT cells was loaded onto HiTrap DEAE FF (5 ml, GE healthcare) and eluted with 20 mM Tris-Cl (pH 8.0) containing 1 M NaCl. 50 μl of supernatant was taken from each collection tubes to test the iDC maturation effect. The collection tubes were selected which showed DC maturation effect and the contents were dialyzed with 20 mM Tris-Cl binding buffer at 4° C. for overnight after freeze drying. The active regions were reloaded onto HiTrap CM FF (5 ml, GE healthcare). Active region were further prepared using cation chromatography (CM), reloaded onto HiTrap Blue HP (1 ml, GE Healthcare) and eluted with 50 mM $KH_2PO_4$ containing 1.5 M KCl (pH 7.0). Final active regions were analyzed for their protein contents with mass spectrometry.

Mass Spectrometric Analysis

Partially purified DC maturation factors from supernatant of CD4+ iNKT cells were loaded onto 12% sodium dodecyl sulfate-polyacrylamide gel electrophoresis (SDS-PAGE) and run at 35 mA for 40 min. The gels were stained using Coomassie Brilliant Blue, G-250 (Boston BioProducts, Worcester, Mass.) before the areas of interest were manually excised and digested 'in-gel' with trypsin, and resulting peptides were spotted onto MALDI target plate (Ferret-Bernard et al., 2008).

A4700 Proteomics Analyzer with TOF-TOF Optics (Applied Biosystems, Framingham, Mass.) was used to obtain MALDI-MS/MS spectra of tryptic peptides in reflector positive mode. Ten most intense peaks in the MS spectrum were automatically selected and were singly charged as this is the dominant species produced by the A4700. MS/MS data from each in-gel digest were processed by GPS Explorer software v3.0 (Applied Biosystems) to provide peak lists containing all masses from 60 up to 20 Da below the precursor mass with a minimum S/N of 20. A protein was considered positively identified if the GPS Explorer total ion score confidence interval exceeded 99.9% (generated by GPS Explorer on the basis of the MASCOT ion scores) and if at least one peptide had a MASCOT expectation value of less than 0.05 meaning that the probability of a random match is less than 0.05. Protein identities were confirmed by searching the National Centre for Biotechnology Information (NCBI) database. The NCBI accession number is given for each match Ferret-Bernard et al., 2008).

DC Generation from Buffy Coats and Maturation Test

Buffy coats obtained from healthy donors according to institutional guideline. PBMC were prepared by density centrifugation using Ficoll-Paque gradient (Amersham Phamacia Biotech, Uppsala, Sweden). $7 \times 10^7$ cells of PBMC were added 10 cm tissue culture plates in 10 ml of RPMI 1640 medium supplemented with 10% heat-inactivated FBS, 2 mM L-glutamine, 100 U/ml penicillin, 10 μg/ml streptomycin, and incubated for 1 hr in 5% $CO_2$ incubator at 37° C.

Nonadherent cells were removed, and the adherent cells were collected with a cell scrapper. In some instances, PBMC were mixed with micro-bead conjugated anti-CD14 antibody (Miltenyi Biotech, Auburn, Calif.) and then incubated on ice for 30 min. After washing with binding buffer (2% FBS, 2 mM EDTA, 20 mM PBS, pH 7.4), $CD14^+$ cells were purified with AutoMACS (Miltenyi Biotech). Purified cells were subsequently cultured in 10 cm culture plates in RPMI 1640 medium supplemented with 10% heat inactivated FBS, 10 mM HEPES, 2 mM L-glutamine, 100 U/ml penicillin, 10 μg/ml streptomycin, 50 μM 2-mecaptoethanol, 5 ng/ml GM-CSF (R &D Systems, Minneapolis, Minn.), and 10 ng/ml IL-4 (R&D). Half of the media were changed on days 3 and 6. To test the DC maturation effect, the nonadherent cells (immature DC) were harvested on day 7 and stimulated with TNF-α or purified supernatants of iNKT cells. The maturation of immature DC was checked with CD86, PDL-1, and HLA-DR on the surface by fluorescence-activated cell sorter (FACS) analysis using the FACSCalibur (BD Bioscience).

Flow Cytometric Analysis

NKT cell clones were phenotypically characterized by using a panel of cell surface antibodies conjugated to fluorescein isothiocyanate (FITC) or phycoerythrin (PE).

Briefly, cells were washed in staining buffer [PBS (pH 7.2) supplemented with 2% FBS and 0.1% sodium azide]. Cells were incubated at 4° C. for 30 min with the appropriate conjugated antibodies and washed twice with staining buffer. FITC conjugated antibodies consisted of CD4, CD8, and immunoglobulin G (IgG) isotype. PE-conjugated antibodies consisted of CD3, CD4, CD8, and NKT (6B11). For assessing maturation of DC, cell markers CD14, HLA-DR, PDL-1, and CD86 were used. Intracellular staining was performed following the manufacturer's recommendations (BD Phamingen). Breldin A solution (1×40 μl per well; BD Biosciences) was added during the last 6-12 h of culture. After staining for the extracellular antigens, cells were incubated with 500 μl of 1× permeabilizing solution 2 (BD Biosciences) for 10 min at room temperature in dark. Isotype-matched control antibodies were included for all experiments as controls for nonspecific binding. Dead cells were gated out by forward and side scatter. Flow cytometry was performed using the FACSCalibur (BD Bioscience) and DATA were analyzed using FlowJo software (TreeStar, Ashland, Oreg.).

Western Blot

Anti-CD3 activated CD4$^+$ iNKT cells were harvested and washed twice ice cold PBS, and the pellet was resuspended in RIPA buffer (50 mM Tris-HCl, pH 7.4, 150 mM NaCl, 1% NP-40, 0.5% Sodium deoxycholate, 0.1% SDS, 5 mM EDTA, 1 mM EGTA, Boston BioProduct, Worcester, Mass.) containing proteinase inhibitor cocktail (Roche Co). After incubation on ice for 30 min, lysates were centrifuged at 14,000 rpm for 10 min and the supernatant was collected for further analysis. 1 vol of Laemmli's sample buffer (4% SDS, 20% glycerol, 10% 2-mecaptoethanol, and 4 mg/100 ml bromophenol blue) was added to the supernatant and incubated at 95° C. for 5 min. The samples were run on 12% SDS-PAGE at 35 mA for 40 min. The supernatant of anti-CD3 activated CD4+ iNKT cells were filtered with 0.2 μm membrane and mixed with Laemmli's sample buffer and then applied on the gel. The proteins from the SDS-PAGE gels were electro-transferred to polyvinylidene difluoride (PVDF) membranes using a transfer buffer containing 25 mM Tris, 190 mM glycine, and 20% methanol at 300 mA for 2 hrs.

After 2 hrs saturation at room temperature in PBS/0.05% Tween 20 containing 5% nonfat milk (Bio-Rad, Hercules, Calif.), membranes were incubated with anti-S100A8 antibody, anti-beta tubulin antibody (1:500, v/v, Cell Signaling Technology, Danvers, Mass.) at 4° C. overnight. Membranes were washed three times with PBS/0.05% Tween 20, and incubated with HRP conjugated anti-mouse IgG (1:1,000, v/v) and anti-rabbit IgG antibody (1:1,000, v/v, Cell signaling) for 1 hr at room temperature. Proteins were detected using Western Lightning® Plus-ECL, Enhanced Chemiluminescence Substrate kit (PerkinElmer, Waltham, Mass.) according to the manufacture's instruction.

Cytokine Assay

The amount of G-CSF, GM-CSF, IL-10, IL-12(p70), IL-1β, IL-2, IL-4, IL-5, IL-6, IL-7, IL-8, IL-17, IFN-γ, MCP-1, MIP-1β, and TNF-α in supernatant of cultured cells were measured with a Bio-Plex pro human cytokine 17-plex assay kit (Bio-Rad, Hercules, Calif.) according to the manufacturer's instructions.

Statistical Analyses

All values are expressed as means±standard deviation. Significant differences between PIP and LPS on DC maturation effect, TLR blocking experiments, and anti-RAGE antibody blocking effect were compared using one-way ANOVA followed by Bonferroni's multiple comparison tests. A P-value of <0.05 was considered to be statistically significant. Statistical significances in T$_{reg}$ generations were determined using t-test with a P value cutoff of 0.05.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Comparison of the Effect of PIP and LPS on DC Maturation

PIP showed similar effect on DC maturation as shown by lipopolysaccharide (LPS) (FIG. 1). CD86, HLA-DR, and PDL-1 on the surface of DC were significantly upregulated by both PIP and LPS (FIG. 1a). Compared to phosphate buffered saline (PBS) both PIP and LPS induced significantly more (twice) maturation of immature DC (FIG. 1b). DC maturation effect of PIP was dependent on PIP concentration (FIG. 1c).

Figure 2:
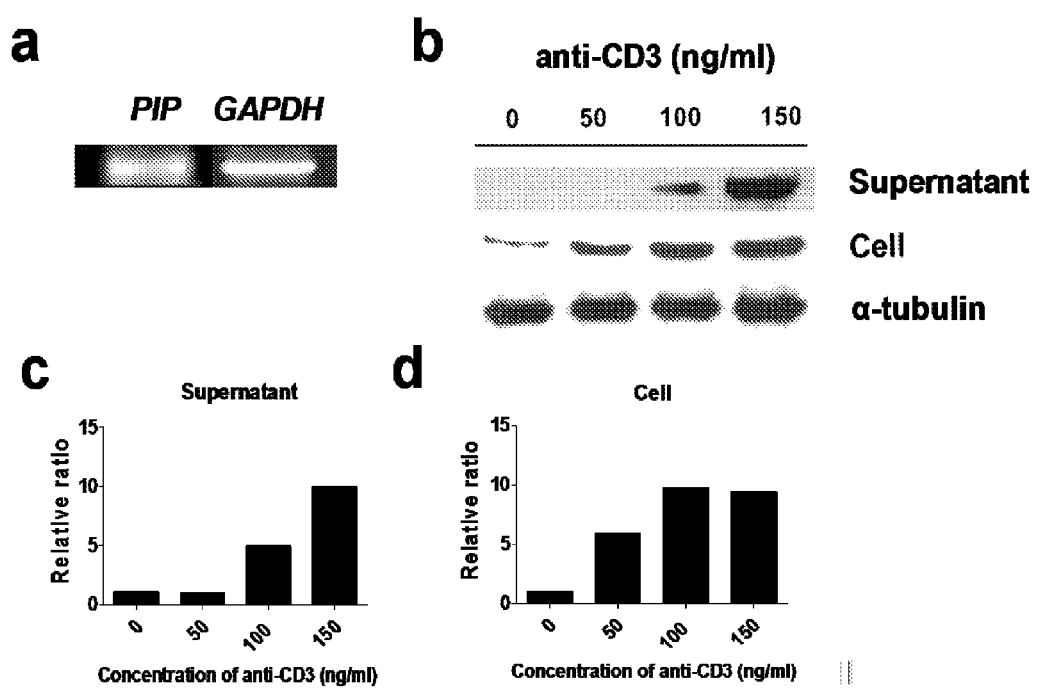
FIGS. 2A-D. Expression of Prolactin induced protein (PIP) in $CD4^+$ iNKT cells and the culture supernatant. (a) RT-PCR, (b) Western blot, (c) relative expressed and secreted levels of PIP, (d) relative expression levels of PIP in cells according to concentration of anti-CD3 antibody. GAPDH: Glyceraldehyde 3-phosphate dehydrogenase.
Figure 3:
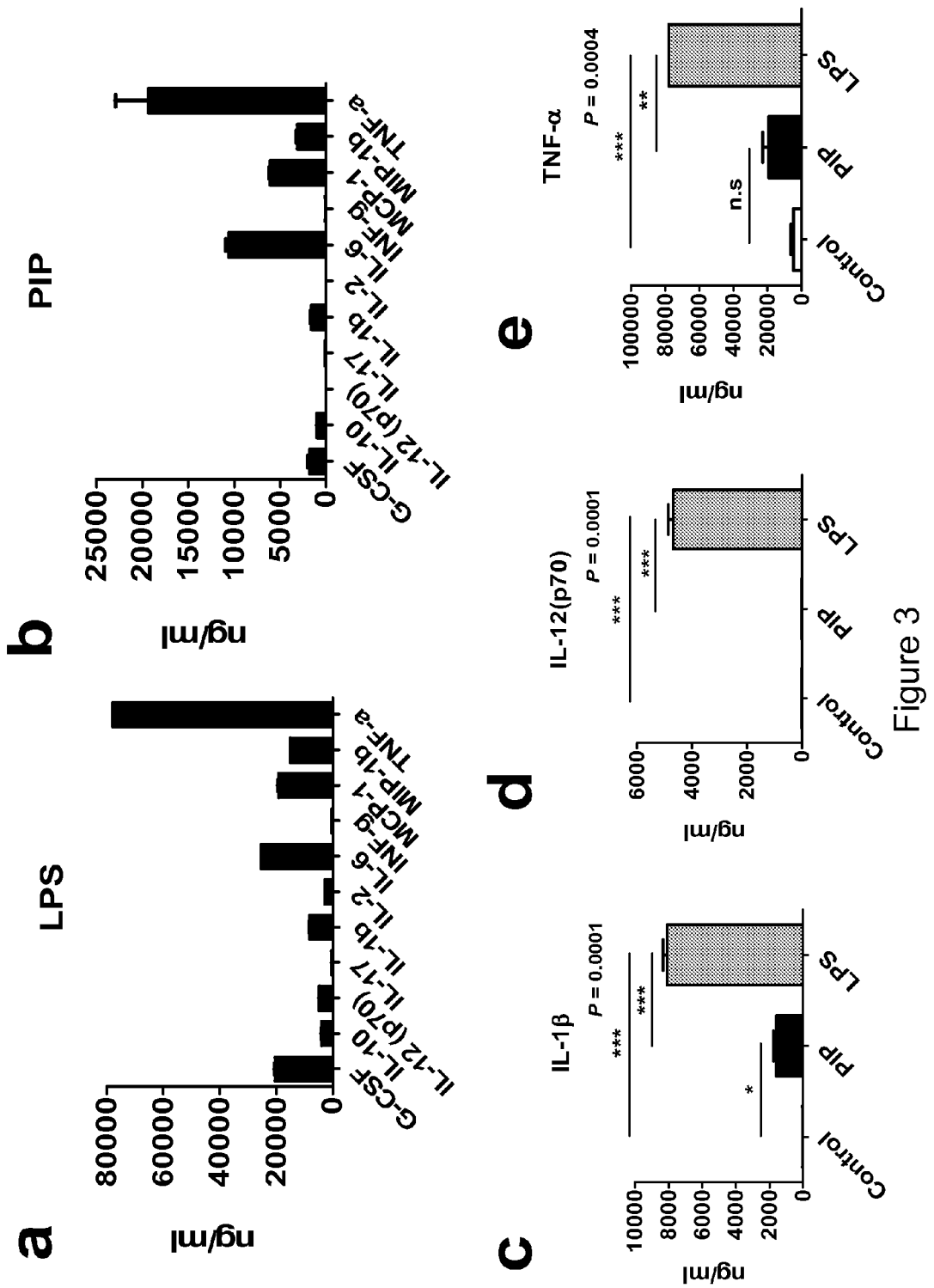
FIGS. 3A-E. Induction of cytokine production by (a) LPS and (b) PIP. Lesser production of pro-inflammatory cytokines in PIP treated iDC, (c) IL-1b, (d) IL-12(p70), and (e) TNF-a. Immature DC were cultured for 48 hours with PIP to allow the induction of tolerogenic DC. Cytokines were analyzed by Bio-Plex pro human cytokine 17-plex assay kit (Bio-Rad). * $P<0.05$;  $P<0.001$; * $P<0.0001$. Error bars indicate mean±s.d.
Figure 4:
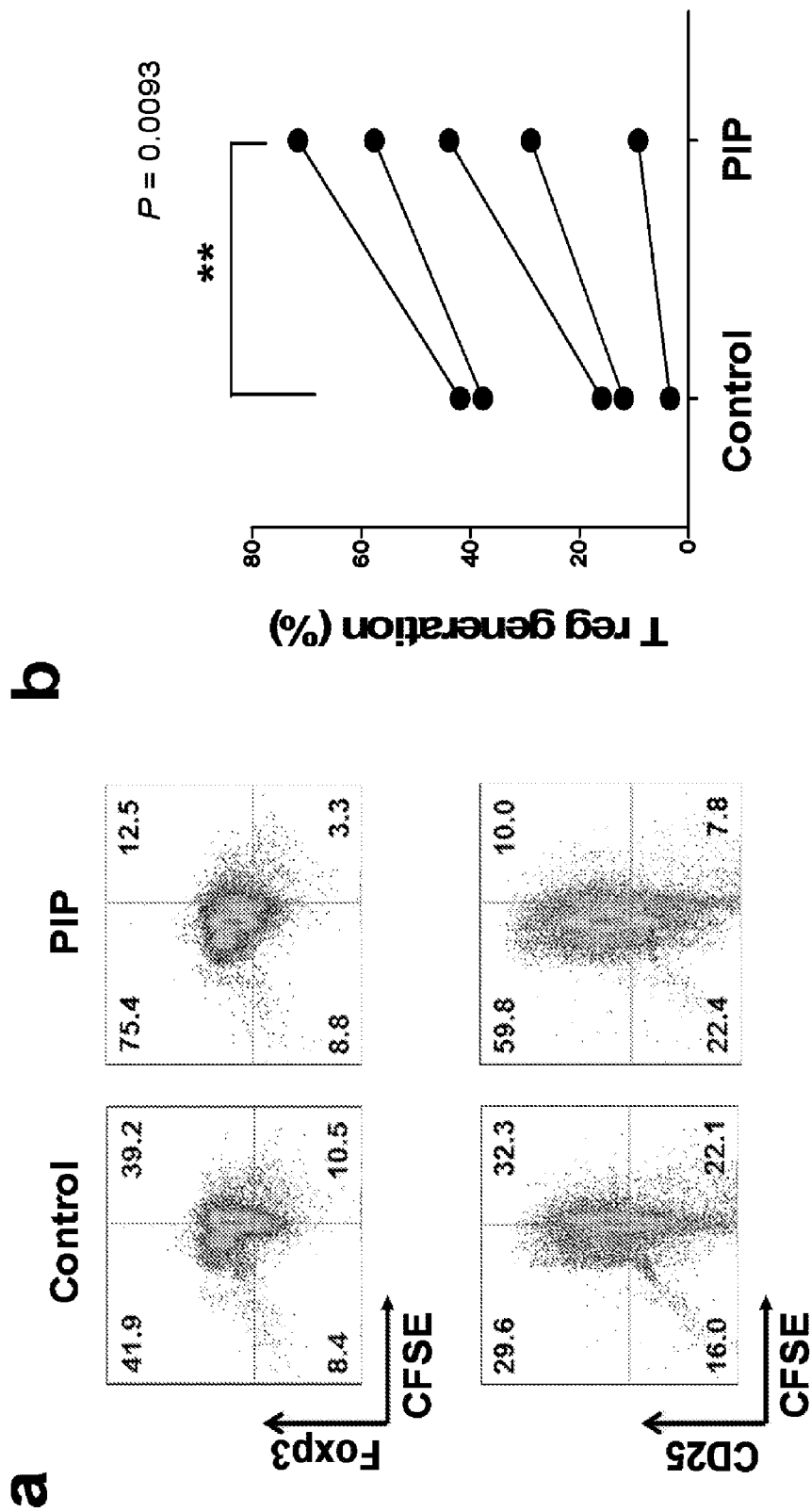
FIGS. 4A-B. Recombinant Prolactin induced protein (PIP) induces $CD4^+CD25^+Foxp3^+$ T ($T_{reg}$) cells. To develop immature DC, $CD14^+$ monocytes were cultured with GM-CSF and IL-4 for 5 days. Immature DC were cultured for 48 hours with PIP to allow the induction of tolerogenic DC. Tolerogenic DC were co-cultured with CFSE labeled $CD4^+CD25^-Foxp3^-$ T cells with 500 ng/ml anti-CD3 antibody, 500 ng/ml anti-CD28 antibody, and 50 U/ml IL-2 for 5 days. Development of $T_{reg}$ cells was assessed by estimating the expression levels of CD4, CD25, and Foxp3 by FACS.
Figure 5:
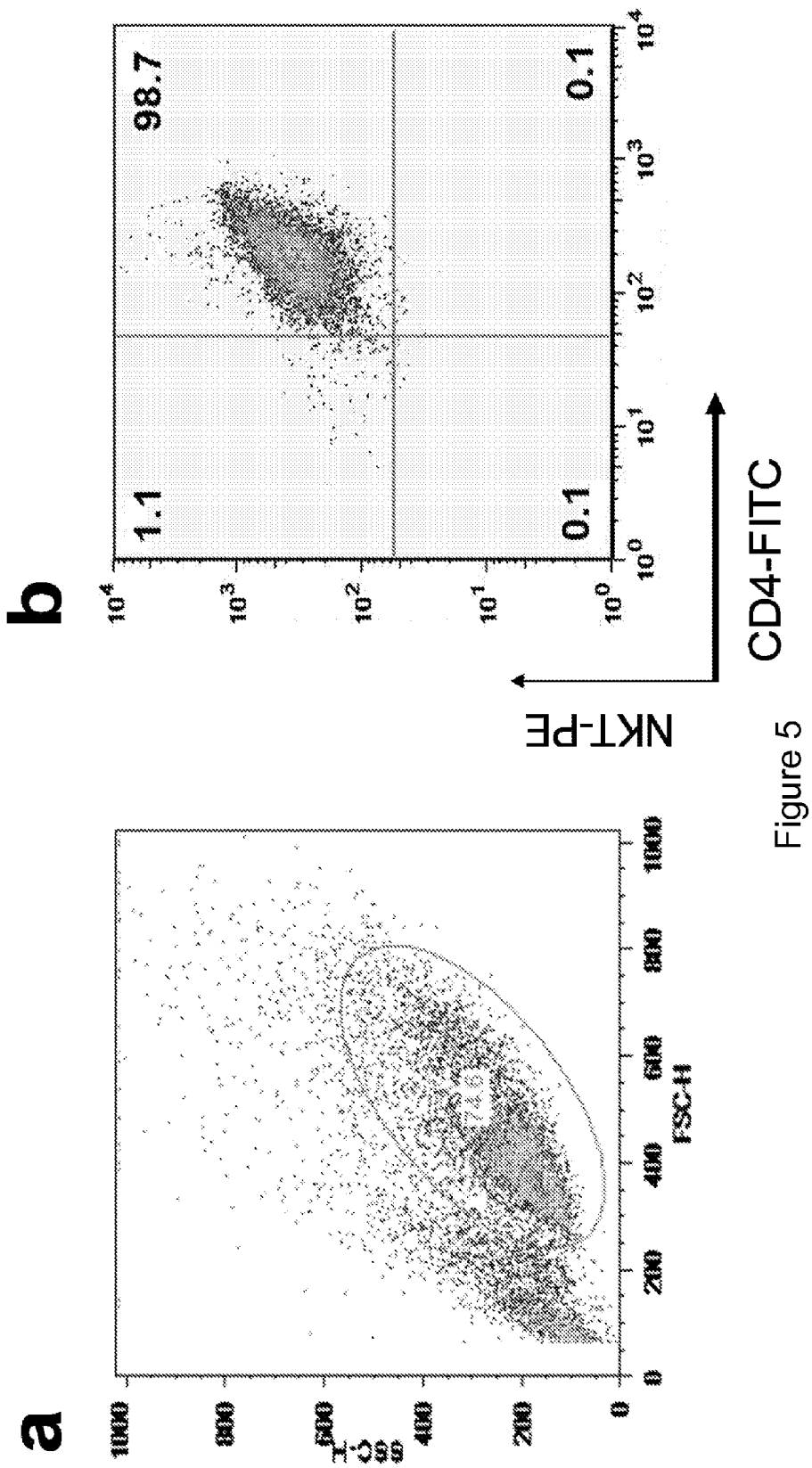
FIGS. 5A-B. Construction of $CD4^+$ NKT cell line. CD1d-restricted T cell clones were generated by single cell sorting using MoFlo from PBMC. Briefly, NKT cells were sorted using the 6B11-fluorochrome conjugated antibody and single-cell sorts were grown with a mixture of irradiated (7500 rad) allogenic peripheral blood mononuclear cells at 75,000 per well, the clones were expanded using anti-CD3 and irradiated PBMC. $CD4^+$ iNKT cell clones were phenotypically characterized by using a panel of cell surface antibodies conjugated CD4 with fluorescein isothiocyanate (FITC) and NKT with phycoerythrin (PE).
Figure 6:
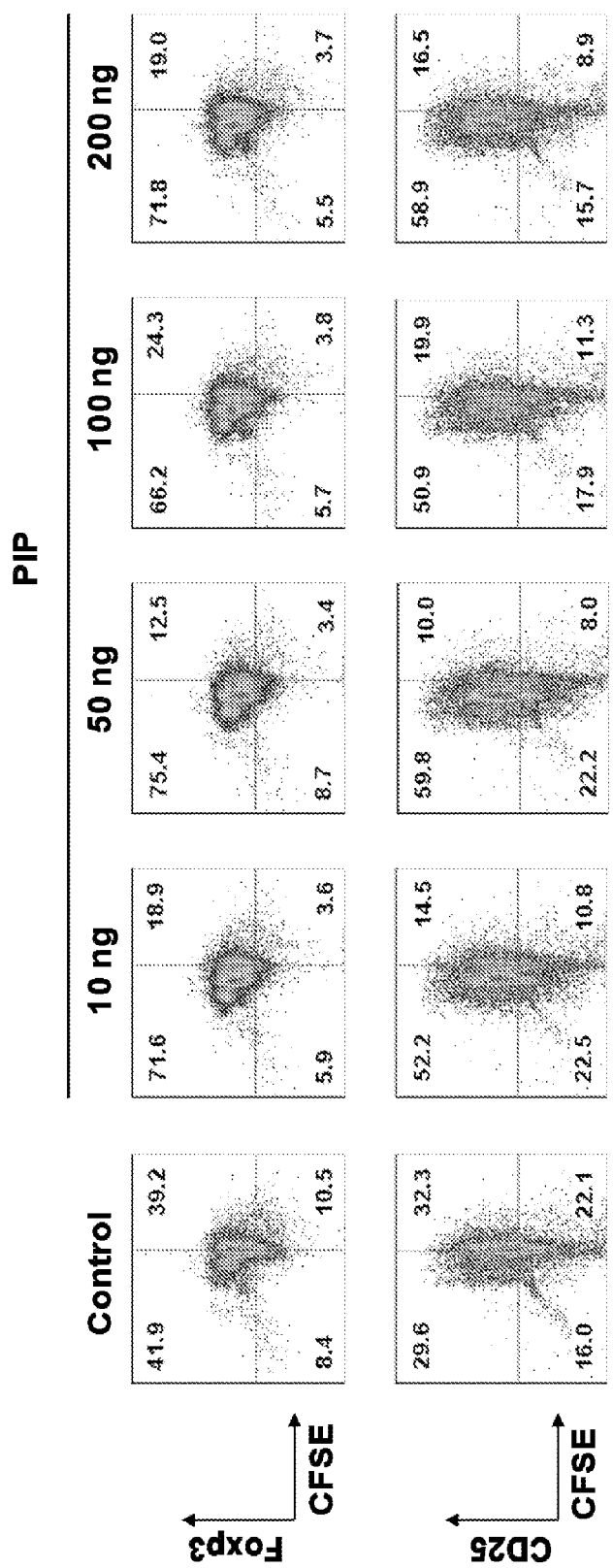
FIG. 6. $T_{reg}$ generation according to various concentrations of recombinant PIP. Tolerogenic DC were induced by treatment with PIP. CFSE labeled $CD4^+CD25^-Foxp3^-$ T cells were added to tolerogenic DC to evaluate the $T_{reg}$ generation by FACS analysis.

Gene expression of PIP in CD4$^+$ iNKT cells was confirmed by reverse transcriptase-polymeric chain reaction (RT-PCR) (FIG. 2a). It was also verified both in the supernatant and the cells by western blot. In the supernatants, expression levels of PIP was increased according to the concentration of anti-CD3 antibody (FIGS. 2b, 2c, and 2d). When the supernatant of DC matured by LPS or PIP were analyzed it was found that IL-4, IL-5, IL-7, IL-8, IL-13, and GM-CSF were not detected in both the groups, i.e. DC stimulated by LPS and PIP. Interestingly, LPS induced much more IL-12 than IL-10 but PIP did reversely (FIGS. 3a and 3b). Pro-inflammatory cytokines, IL-1β, IL-12, and TNF-α were significantly increased by LPS but not by PIP (FIGS. 3c, 3d, and 3e). DC matured by treatment with PIP induced the production of CD4$^+$CD25$^+$Foxp3$^+$ T cells from naïve T cells at a significantly higher rate than control (FIGS. 4a and 4b). Even a small amount of PIP (10 ng) could induce CD4$^+$CD25$^+$Foxp3$^+$ T cells (FIG. 6).

Example 2—PIP Signaling for DC Maturation

The generation of T$_{reg}$ cells by CD4$^+$ iNKT cells is intriguing because it offers an explanation for the immunoregulatory functions of iNKT cells in inflammatory diseases. Therefore, CD4$^+$ iNKT cells may regulate the differentiation of pro-inflammatory T$_H$1 and T$_H$17 cells by generating T$_{reg}$ cells.

Recombinant PIP recapitulates function, and both purified and recombinant induction of DC differentiation is blocked by anti-TLR2 but not by anti-TLR1, 2, 4, 5, 6, 9 antibodies and anti-RAGE antibody. Interestingly, PIP induced CD4$^+$CD25$^+$Foxp3$^+$ T cells (T$_{reg}$) from naïve T cells and reduced T$_H$1 and T$_H$17 cells produced by Pam3CSK. Therefore, PIP is a strong factor by which iNKT regulate immune response through TLR2.

Figure 7:
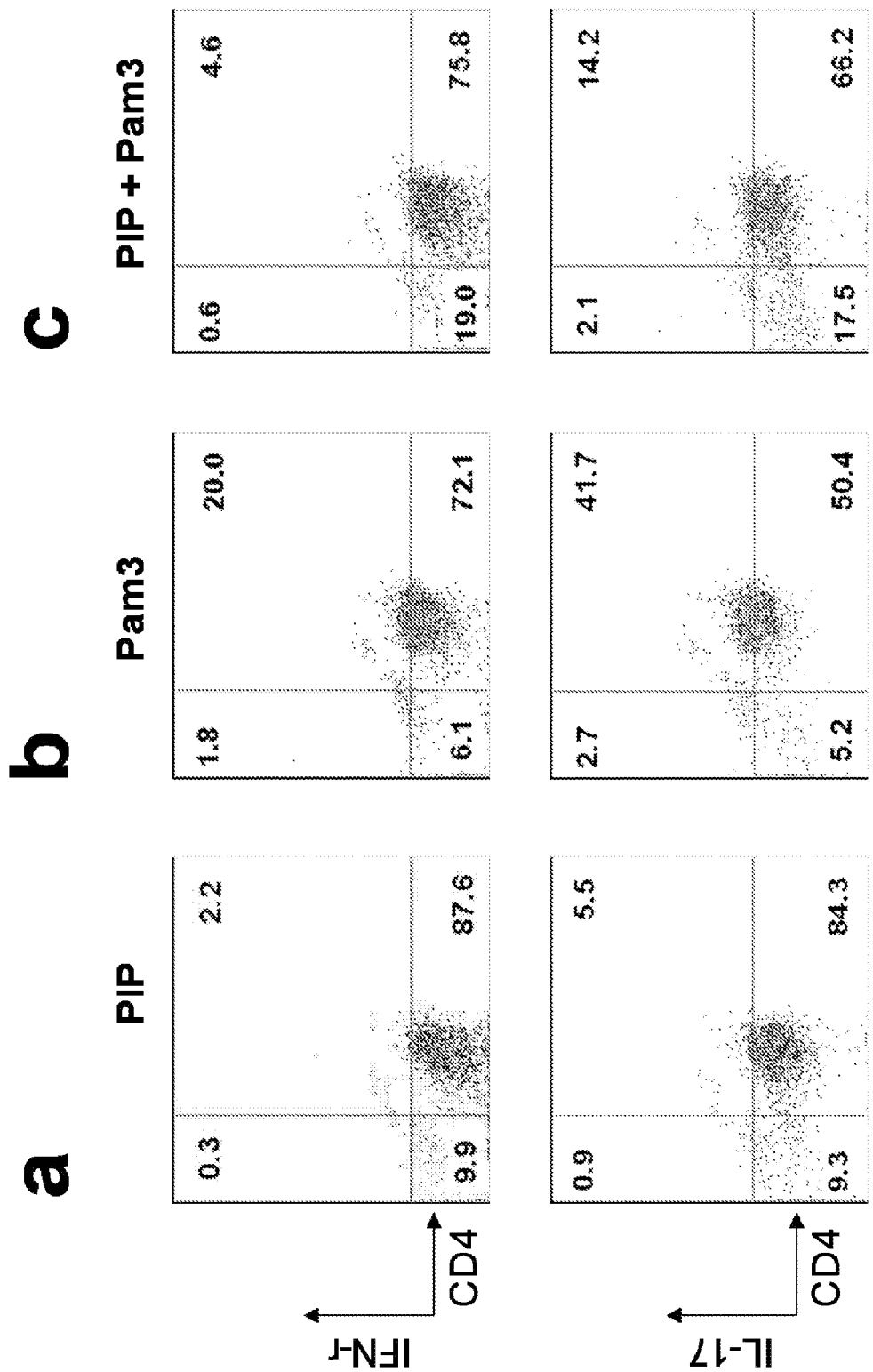
FIGS. 7A-C. Affect of PIP on cytokine profiles of naïve T cells matured in the presence PIP, Pam3, or the combination of both. Tolerogenic DC were induced by treatment with PIP, Pam3, or PIP and Pam3. CFSE labeled $CD4^+CD25^-Foxp3^-$ T cells were added to tolerogenic DC to evaluate the cytokine secretory profiles by FACS analysis.
Figure 8:
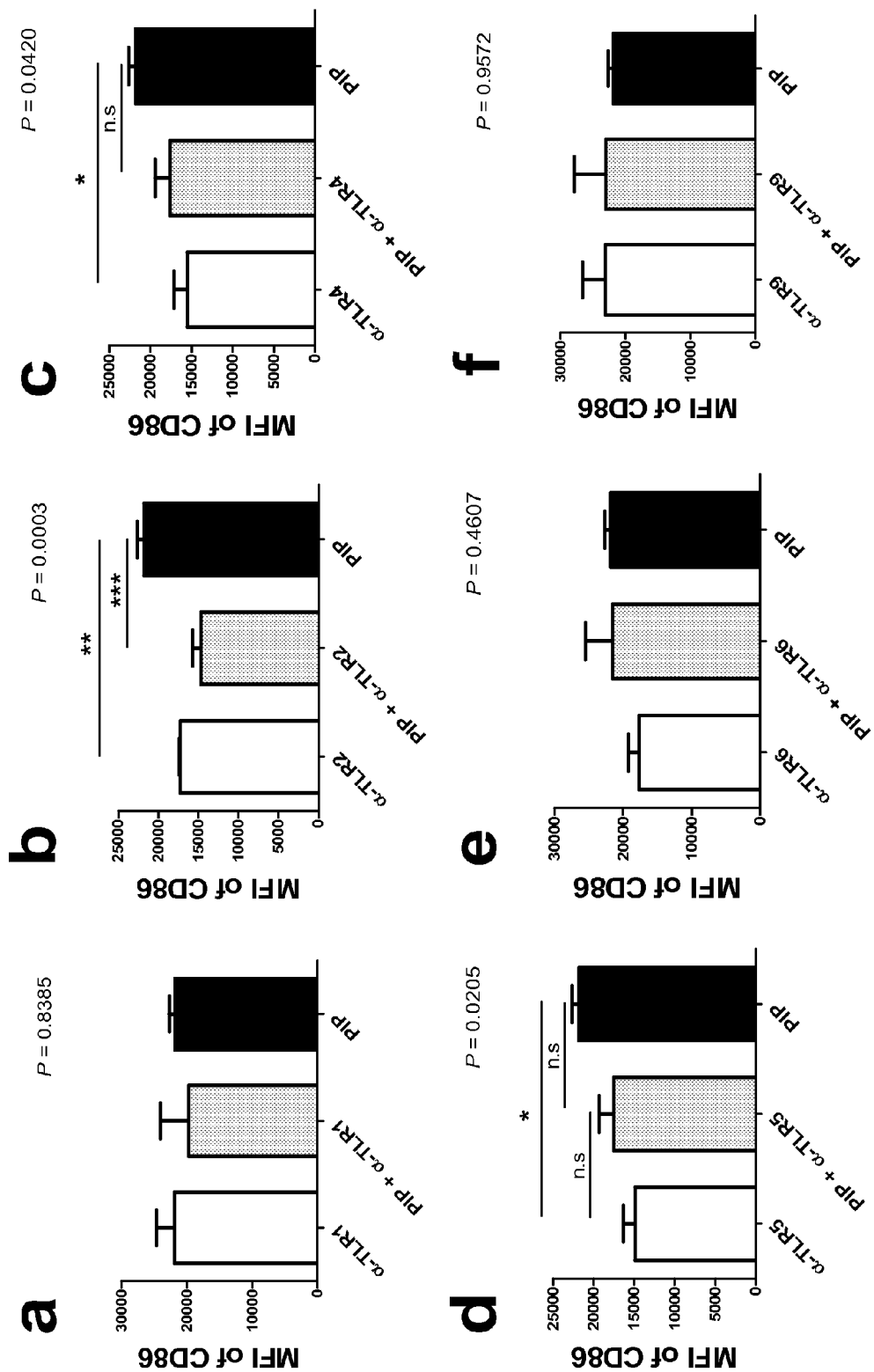
FIGS. 8A-F. Blocking effect of anti-TLR antibodies on DC maturation. 1 μg/ml of anti-TLR antibodies were pre-cultured with immature DC for 1 hr before adding 500 ng/ml recombinant PIP. The maturation of immature DC was assessed by estimating the expression level of CD86 on the DC surface by FACS. * $P<0.05$. * $P<0.01$, *** $P<0.001$. Results are representative of three independent experiments. Error bars indicate mean±s.d.
Figure 9:
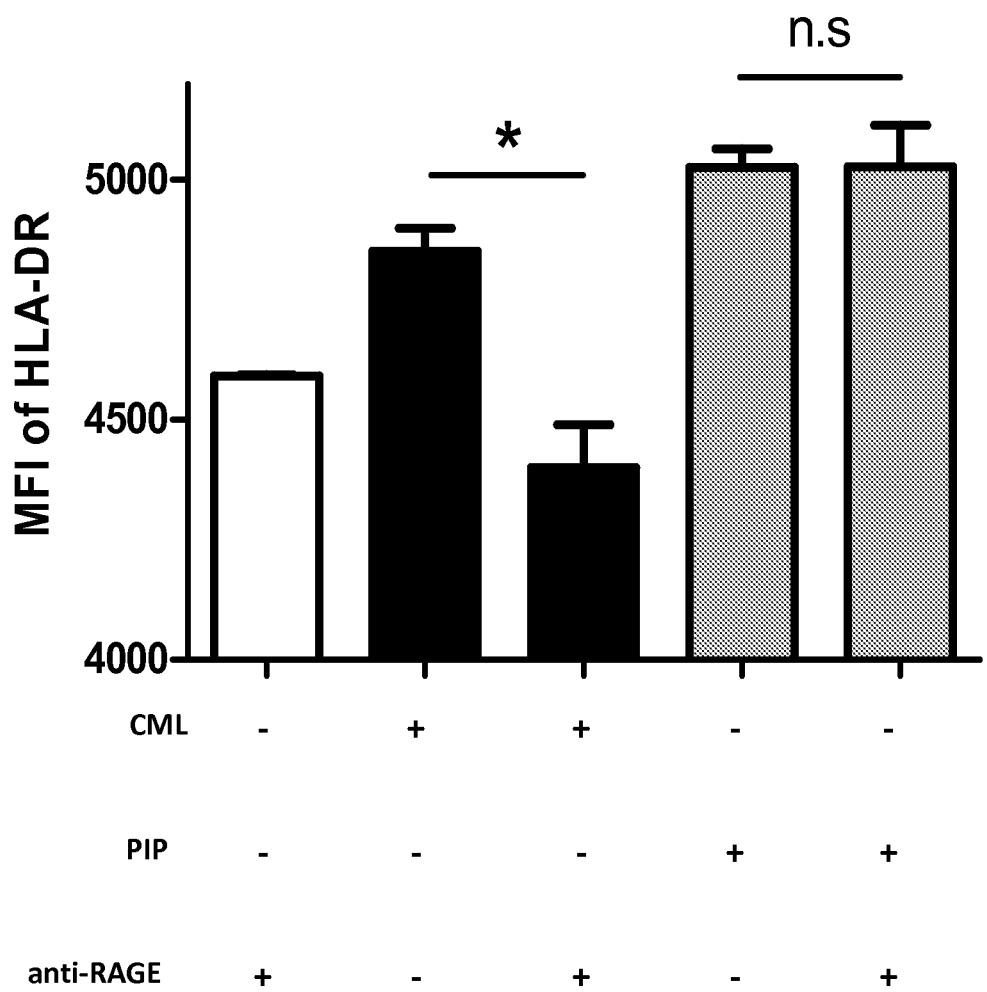
FIG. 9. Blocking effect of anti-RAGE antibody on DC maturation. 1 μg/ml of anti-RAGE antibody was pre-cultured with immature DC for 1 hr before adding 500 ng/ml recombinant PIP. The maturation of immature DC was assessed by estimating the expression level of HLA-DR on the DC surface by FACS. * $P<0.05$. Results are representative of three independent experiments. Error bars indicate mean±s.d.

The inclusion of PIP and Pam3CSK4, synthetic bacterial lipoprotein-TLR2-TLR1 ligand, treated DC with CD4$^+$CD25$^-$Foxp3$^-$ T cells significantly suppressed the differentiation of T$_H$1 and T$_H$17 cells (FIG. 7). These data indicate that CD4$^+$ iNKT cells induce T$_{reg}$ cells, which subsequently suppress T$_H$1 and T$_H$17 development even under pro-inflammatory conditions. It was suggested that Foxp3 transcriptionally suppresses T$_H$1 and T$_H$17 cell differentiation (Hori et al., 2003). However, the data provided here suggest the possibility that at the cellular level, T$_{reg}$ cells can suppress the differentiation of pro-inflammatory T$_H$1 and T$_H$17 cells. It is known that S100A8 binds the receptor for advanced glycation end products (RAGE) and toll like receptor 4 (TLR4) (Vogl et al., 2007). However, DC maturation by PIP was not blocked by adding anti-TLR4 antibody (FIG. 8c). $N^C$-carboxymethyllysine (CML), agonist of RAGE did not induce the DC maturation and anti-RAGE antibody did not inhibit the maturation effect of PIP (FIG. 9). However, CD86 expression of DC was reduced by anti-TLR2 antibody (FIG. 8b). These findings suggest that PIP regulates DC maturation via TLR2 signaling.

Figure 10:
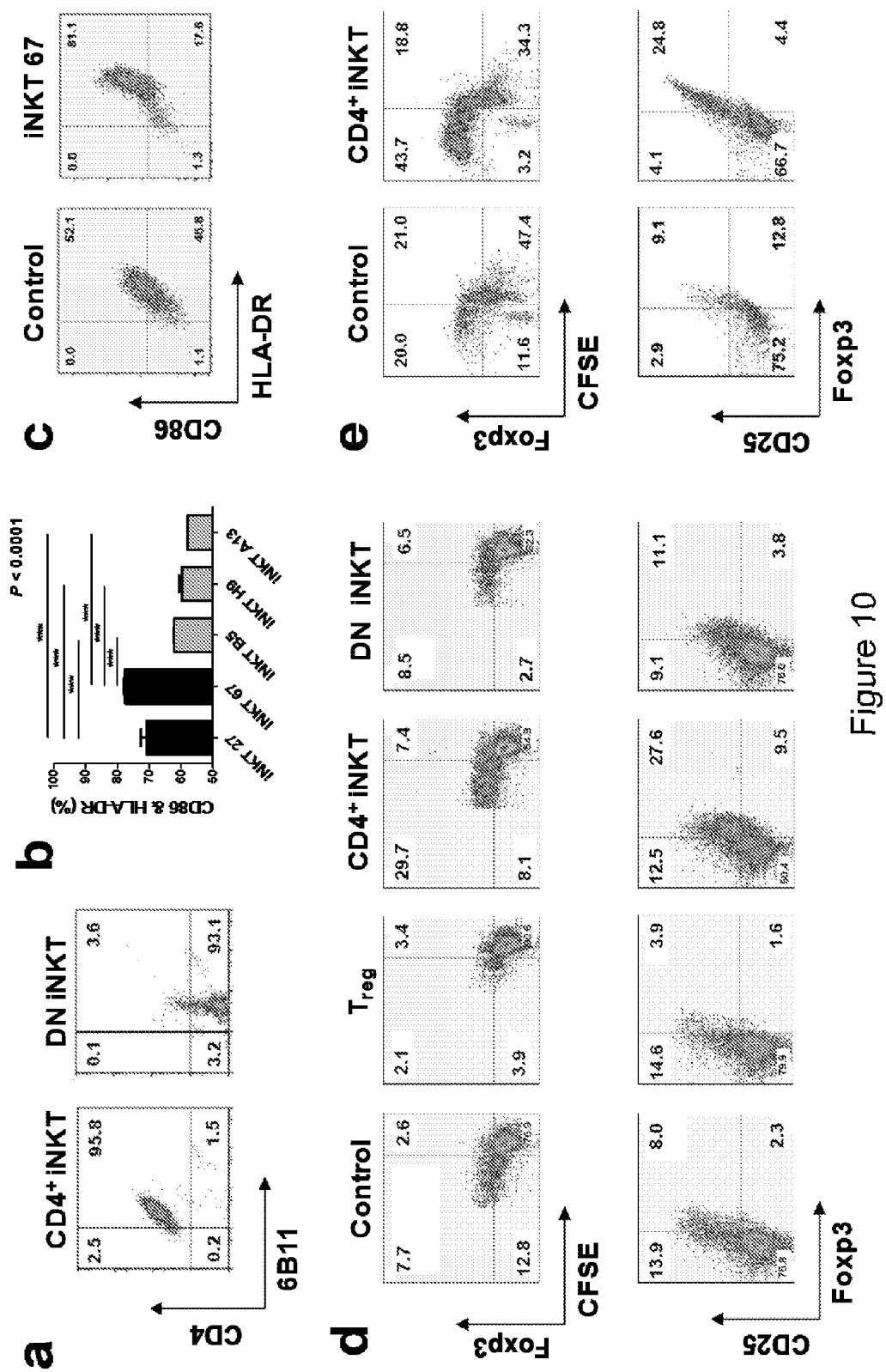
FIGS. 10A-E. Comparison of the induction of DC maturation by $CD4^+$ and double negative iNKT cells. (a) FACS profile of representative $CD4^+$ and double negative (DN) iNKT cells. (b) Human immature dendritic cells differentiated into mature dendritic cells by addition of supernatant from anti-CD3 antibody activated $CD4^+$ iNKT cells and DN iNKT cells. Data obtained from triplicate experiments with each clones. (c) Representative FACS profile of maturation of dendritic cell by PBS only (control) and the supernatant of $CD4^+$ iNKT 67. Immature DC were generated as described in materials and methods. (d) $CD4^+$ iNKT cells caused more Foxp3 and CD25 expression compared to that caused by DN iNKT cells. (e) Immature DC were matured by supernatant of $CD4^+$ iNKT cell through the transwell. After 4 days of stimulation with anti-CD3 and anti-CD28 antibodies, $CFSE^+CD4^+$T cells were analyzed for Foxp3 and CD25 expression. Data shown are representative of three independent experiments. Significant differences were evaluated by one-way ANOVA followed by Bonferroni's multiple comparison tests. *** $P<0.0001$. Error bars indicate mean±s.d.

Example 3—CD4$^+$ iNKT Cell Induces Dendritic Maturation iNKT cells were isolated from peripheral blood mononuclear cells (PBMC) of healthy volunteers using 6B11 antibody and microbead conjugated anti-IgG1 antibody. CD4$^+$ and double negative (DN) iNKT cells were separated with CD4 microbead (FIG. 10). To prepare the supernatant of anti-CD3 antibody activated CD4$^+$ and DN iNKT cells, the cells were washed with RPMI 1640 medium three times and applied onto 100 ng/ml anti-CD3 bounded plate and then cultured with 50 U/ml of IL-2. Supernatants were collected and added to immature DC. Immature DC were induced from monocytes, freshly purified from human peripheral blood by CD14 magnetic sorting and incubating with granulocyte-macrophage colony-stimulating factor (GM-CSF) and IL-4. After 48 hours, the surface markers, HLA-DR and CD86, were measured by FACS. Those markers were much more upregulated by adding the supernatant of CD4$^+$ iNKT cells (iNKT 27 and iNKT 67) compared to adding the supernants from DN iNKT cells (iNKT B5, iNKT H9, and iNKT A13) (FIGS. 10b, 10c).

Example 4—CD4$^+$ iNKT Cell Generates Regulatory T Cell and Inhibits $T_H1$ and $T_H17$ Cell Development iNKT cell subsets were tested for their capacity to convert CD4$^+$CD25$^-$Foxp3$^-$ T cells into CD4$^+$CD25$^+$Foxp3$^+$ T cells in a series of in vitro reconstitution experiments. Co-culture of CD4$^+$CD25$^-$Foxp3$^-$ T cells with DN iNKT cells resulted in much less expression of CD25 or Foxp3 when compared with CD4$^+$ iNKT cells (FIG. 10d). Since iNKT cells are thought to control myeloid antigen presenting cell (APC) effector function and thereby regulate T cell differentiation (Vincent et al., 2002; Wilson et al., 2003), the co-culture experiments were repeated with the addition of autologous CD14$^+$-derived APC. iNKT cell-dependent conversion was markedly enhanced by the inclusion of myeloid APC, and the conversion was more effective when CD4$^+$ rather than DN iNKT cell lines were used. Additionally, the $T_{reg}$ generation by the CD4$^+$ iNKT cells was not caused by cell-to-cell contact (FIG. 10e).

Figure 11:
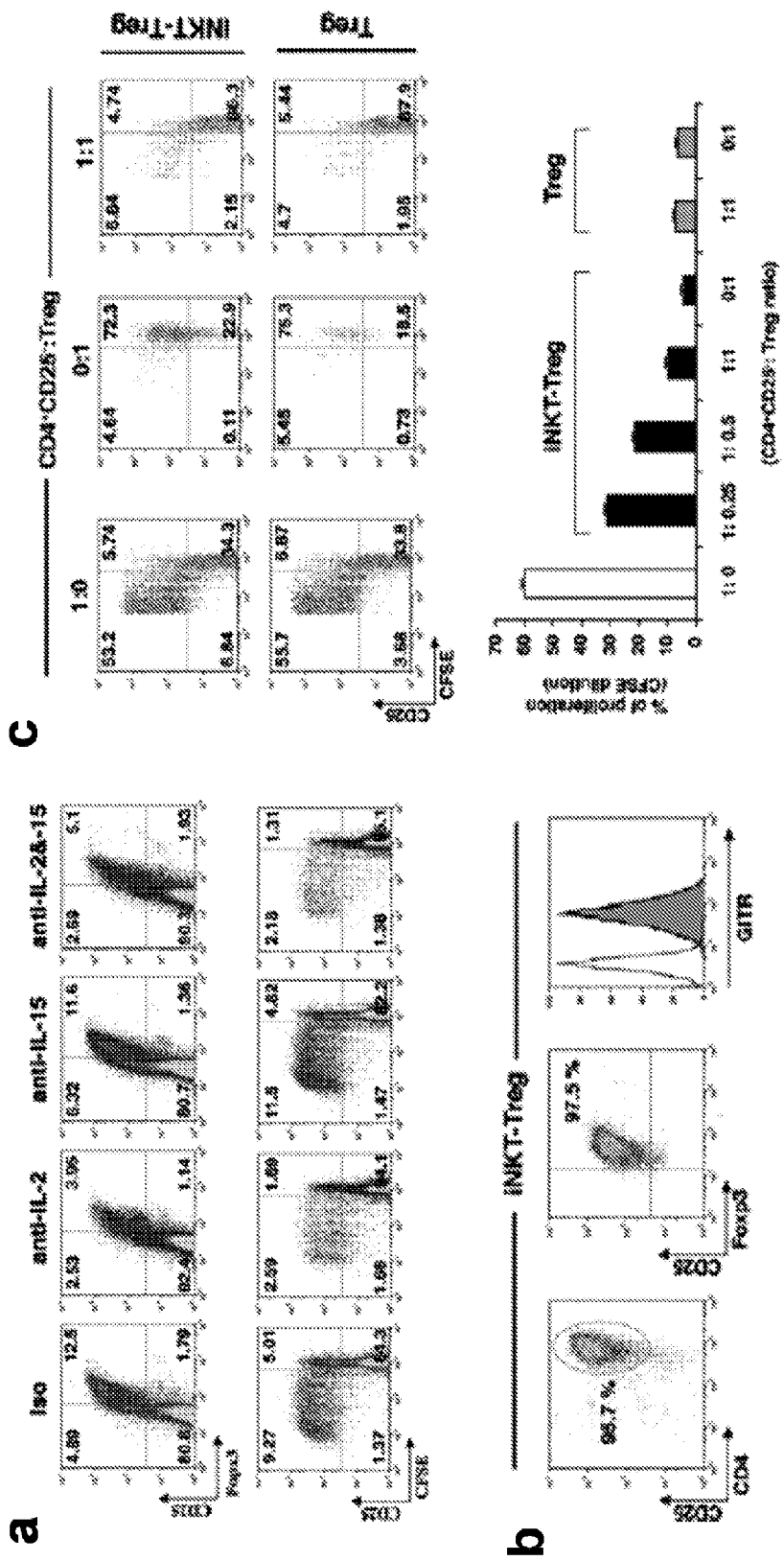
FIGS. 11A-C. $CD4^+$ iNKT cells selectively generate functional $T_{reg}$ ($CD4^+CD25^+Foxp3^+$) from non-$T_{reg}$ ($CD4^+CD25^-Foxp3^-$) cells in an IL-2 and APC dependent manner. (a) CFSE-labeled PBMCs were stimulated with α-GalCer in the presence of neutralizing antibodies as indicated, for five days. $CD4^+$ T cells (gated at 6B11−) were analyzed for the percentage of $CD4^+CD25^+Foxp3^+$ cells and CFSE dilution. (b) Established iNKT-$T_{reg}$ cells were analyzed for their purity, Foxp3, CD25, and GITR expression. (c) CFSE-labeled $CD4^+CD25^-$ T cells were stimulated with anti-CD3 and anti-CD28 antibodies plus $CD14^+$ APC in the absence (white bar) or presence of iNKT-$T_{reg}$ (black bars) or $CD4^+CD25^+$ T cell (gray bars) for 4 days. CFSE-labeled $T_{reg}$ or iNKT-$T_{reg}$ cells were also stimulated by anti-CD3 and anti-CD28 antibodies plus $CD14^+$ APC. $CFSE^+$ cells were analyzed for proliferation by CFSE dilution. Graphs are shown as the mean±s.d. of triplicate. Results shown here are representatives of three experiments.
Figure 17:
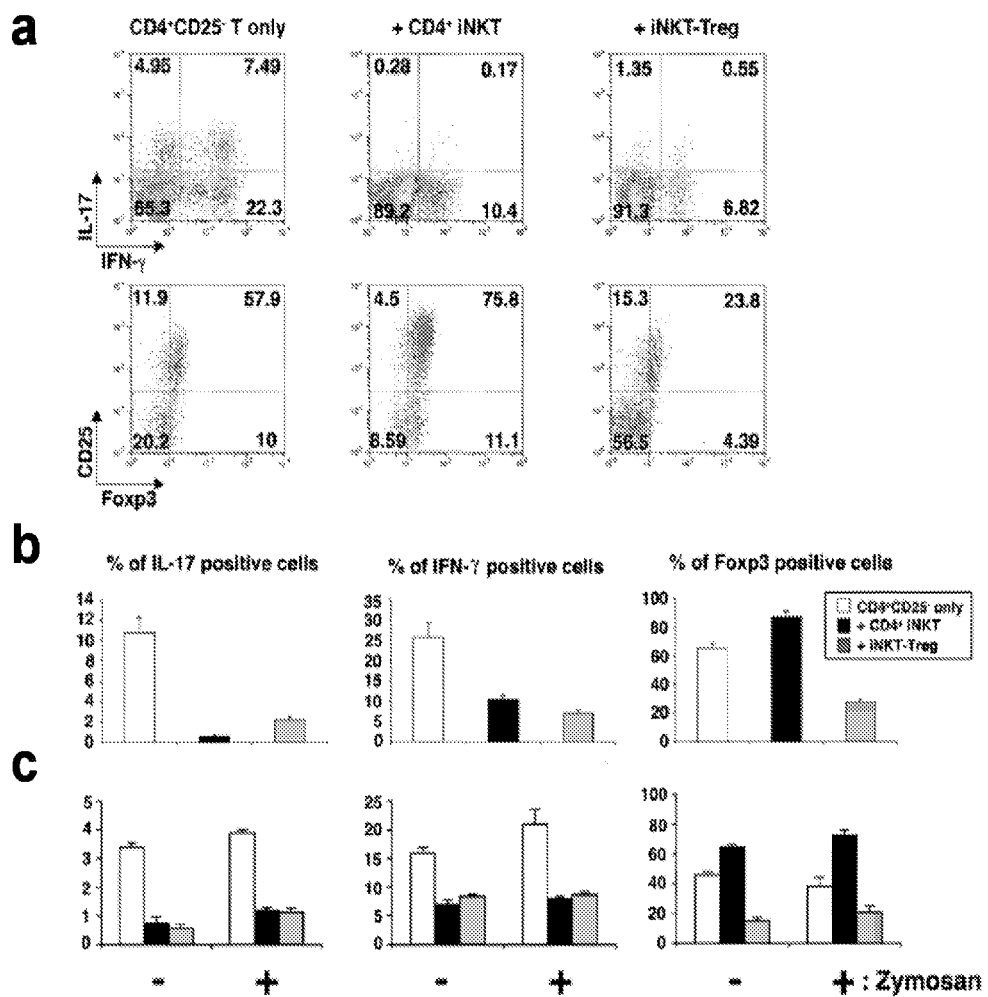
FIGS. 17A-C. CD4+ iNKT cells suppress $T_H1$ and $T_H17$ cell differentiation by generating $T_{reg}$. (a, b) CFSE-labeled CD4+CD25- T cells were stimulated with anti-CD3 and anti-CD28 antibodies plus CD14+ APC in the presence or absence of CD4+ iNKT or iNKT-$T_{reg}$ cells for 5 days. CFSE+CD4+ T cells were analyzed for IFN-γ, IL-17, Foxp3 or CD25 expression. (c) The same culture conditions used in (b) were repeated in the presence or absence of zymosan. Graphs are shown as the mean±s.d. of triplicate. Results shown here are representatives of three experiments.

Interestingly, α-Galactosylceramide (GalCer) stimulation resulted in an expansion of CD4$^+$CD25$^+$Foxp3$^+$ T cells from non-iNKT (6B11$^-$)CD25$^-$ CD4$^+$ T cells (FIG. 11a). As observed for iNKT cell expansion, IL-2 neutralization suppressed the expansion of CD4$^+$CD25$^+$Foxp3$^+$ T cells in response to α-GalCer while IL-15 neutralization did not. These results indicate that IL-2 secreted by α-GalCer-stimulated iNKT cells enhanced the expansion of CD4$^+$CD25$^+$Foxp3$^+$ T cells. Strikingly, iNKT cell-dependent conversion was markedly enhanced by the inclusion of myeloid APC, and the conversion was 3-5 fold more when CD4$^+$ rather than DN iNKT cell lines were used. Due to the phenotypic similarity with $T_{reg}$ cells, the CD4$^+$CD25$^+$Foxp3$^+$ T cells converted by CD4$^+$ iNKT cells were designated as iNKT-$T_{reg}$ cells (FIG. 11b). iNKT-$T_{reg}$ cells were tested for their suppressive activity on the proliferation of CD4$^+$CD25$^-$ T cells. Indeed, iNKT-$T_{reg}$ cells effectively suppressed the proliferation of CD4$^+$CD25$^-$ T cell as efficiently as $T_{reg}$ cells (FIG. 11c). The generation of $T_{reg}$ cells by CD4$^+$ iNKT cells is intriguing because it offers an explanation for the immunoregulatory functions of iNKT cells in inflammatory diseases. Therefore, CD4$^+$ iNKT cells may regulate the differentiation of pro-inflammatory $T_H1$ and $T_H17$ cells by generating $T_{reg}$ cells. The inclusion of CD4$^+$ iNKT cells or iNKT-$T_{reg}$ with CD4$^+$CD25$^-$Foxp3$^-$ T cells plus CD14$^+$-derived APC significantly suppressed the differentiation of $T_H1$ and $T_H17$ cells (FIGS. 17a, 17b). Importantly, even under conditions that efficiently induced $T_H1$ and $T_H17$ cell development, the inclusion of CD4$^+$ iNKT cells suppressed this pathway and skewed the outcome towards the development of CD4$^+$CD25$^+$Foxp3$^+$ T cells, whilst iNKT-$T_{reg}$ suppressed all forms of differentiation (FIG. 17c). Hence, these data indicate that CD4$^+$ iNKT cells induce $T_{reg}$ cells, which subsequently suppress $T_H1$ and $T_H17$ development even under pro-inflammatory conditions. It was suggested that Foxp3 transcriptionally suppresses $T_H1$ and $T_H17$ cell differentiation (Hori et al., 2003). However, the data provided here suggest that at the cellular level, $T_{reg}$ can suppress the differentiation of pro-inflammatory $T_H1$ and $T_H17$ cells.

Figure 18:
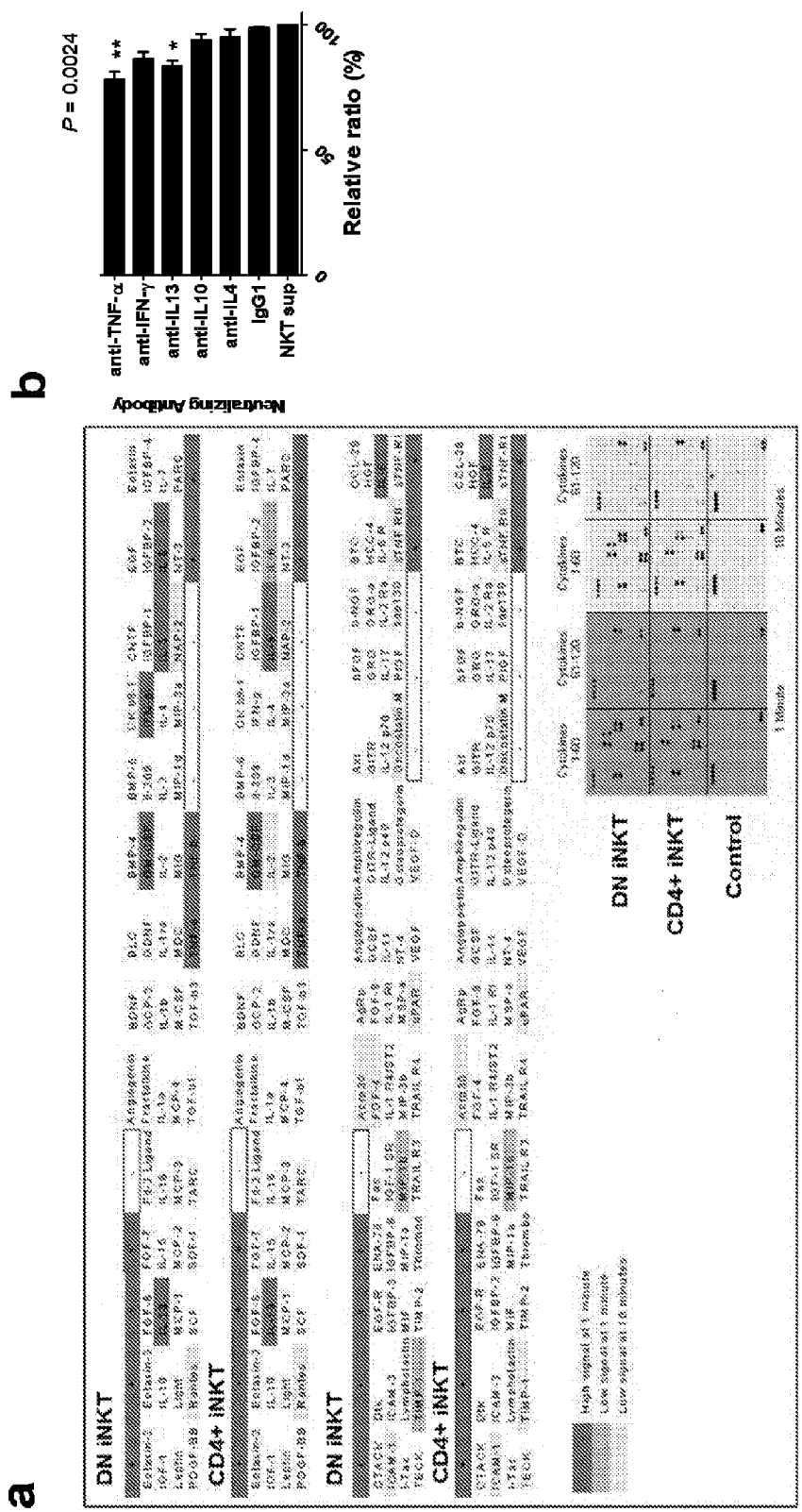
FIGS. 18A-B. Blocking effect of several antibodies on dendritic cell maturation. (a) Cytokine profiling for representative CD4+ and DN iNKT cells. Cytokine profiles were taken of culture supernatant from a CD4+ iNKT cells and a DN iNKT cells 24 hours post stimulation with anti-CD3 antibody. Culture supernatants were assayed in duplicate and assessments made for both one and ten minute exposures. Signals were scored as high, low or absent. A "+" indicates a positive control; a "−" indicates a negative control. (b) Culture media of CD4+ iNKT cells (NKT sup) efficiently induced the maturation of immature dendritic cells (iDC). To test the blocking effect of several antibodies on iDC maturation, the nonadherent cells (iDC) were harvested on day 7 and added supernatant of CD4+ iNKT cells and/or anti INF-γ, anti TNF-α, anti IL-4, anti IL-10, anti IL-13, and IgG1. The maturation of immature DC was assessed by estimating expression levels of HLA-DR on the DC surface by FACS. The relative maturation effect of supernatants of anti-CD3 antibody activated CD4+ iNKT cells was set as 100%. The addition of antibody against TNF-α and IL-13 significantly decreased the maturation of iDC by CD4+ iNKT cells culture medium (P<0.05). On the other hand, the addition of anti IL-4 and IL-10 antibodies showed no inhibitory effect on dendritic cell maturation. * $P<0.05$; ** $P<0.001$. Results are representative of three independent experiments. Error bars indicate mean±s.d.

Example 5—Neutralizing Antibodies of Several Cytokines Did not Block the DC Maturation Human and murine iNKT cells have been implicated in the differentiation of tolerogenic myeloid DC subsets (Hedge et al., 2007; Vincent et al., 2002) and that the phenotype of CD4$^+$ iNKT cells seems to be an anti-inflammatory profile (Hedge et al., 2010; Mars et al., 2009). It is interesting that the supernatants of activated CD4$^+$ iNKT have the ability to induce myeloid DC differentiation. To characterize CD4$^+$ and DN iNKT cells it was important to ascertain what cytokines these cell types secrete upon activation. We used the same pair of iNKT cells, CD4$^+$ and DN, and drew supernatant at 24 hours (given that the 4 hour time point that was considered to be too early to be representative of activated cells). When assayed for 120 different cytokines (FIG. 18a), both iNKT cells made the inflammatory mediator ICAM (Hayflick et al., 1998; Takahashi et al., 2006) and tissue inhibitor of metalloprotease 1 (TIMP1) (Contasta et al., 1999) as well as IL-5, IL-6, and the inflammatory cytokine IL-8. Of these TIMP1, and IL-8 have not been described before as being produced by iNKT cells. Additionally, the iNKT cells differed in that the DN cells made INF-γ while the CD4$^+$ cells did not produce IFN-γ. The majority of cytokines and chemokines from iNKT cells, GM-CSF, IL-4, MIP-1α, and, MIP-1β, are more important for early maturation of myeloid DC and IL-10, IL-13, and IFN-γ showed regulating effector function than for inducing terminal differentiation (FIG. 18a). Therefore, we have examined the supernatants of stimulated CD4$^+$ and DN iNKT cells and have not been able to discern any significant differences when comprising the levels of these cytokines secreted into the media. The addition of anti-IL-4, -10, -13, IFN-γ, and TNF-α monoclonal antibodies (mAb) did not inhibit fully the effect of culture medium of CD4$^+$ iNKT cells, and combinations of mAbs did not abrogate the differentiation (FIG. 18b). However, we could not find reasonable candidates for DC maturation. Therefore, we investigated dendritic cell maturation factors originated from supernatant CD4$^+$ iNKT cell using Mass spectrometry.

Figure 19:
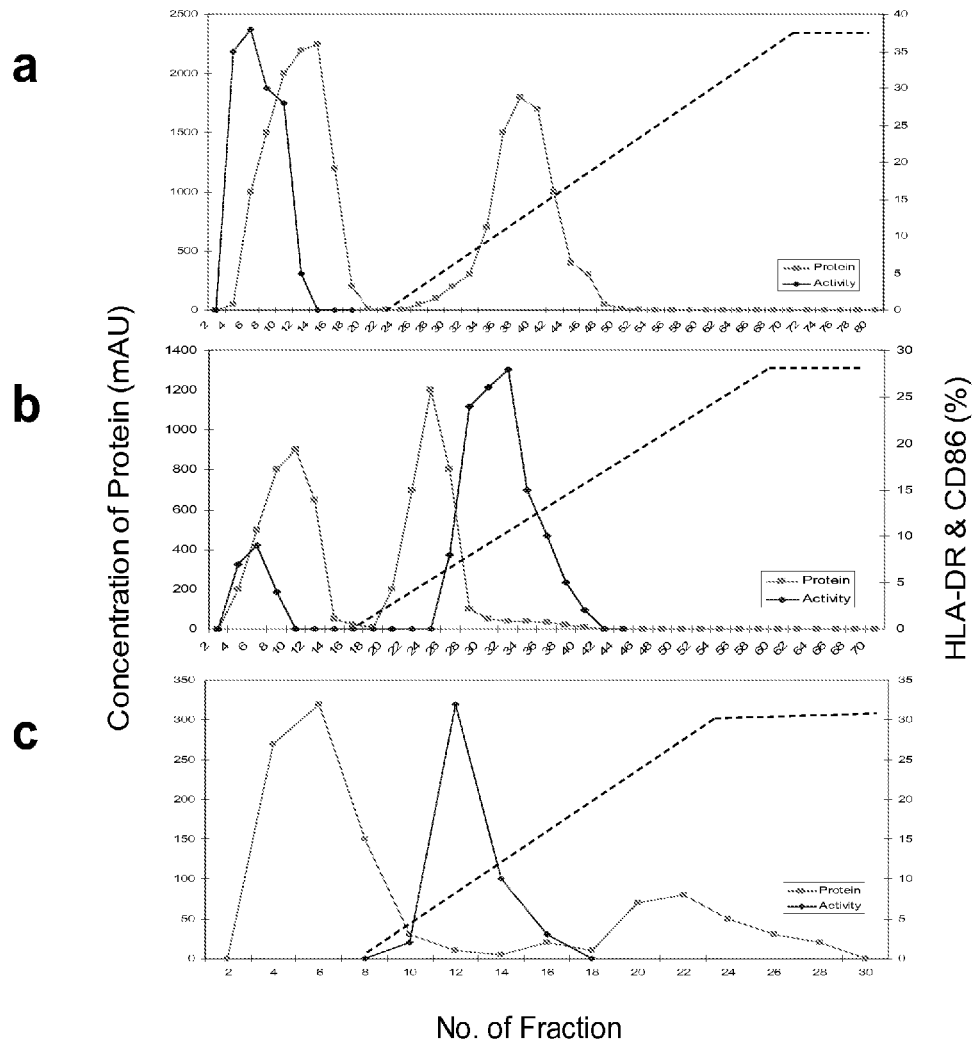
FIGS. 19A-C. The purification steps of DC maturation factors secreted by CD4+ iNKT cells with FPLC chromatography. (a) Anti-CD3 antibody activated supernatants of CD4+ iNKT cells were loaded onto HiTrap DEAE FF and eluted with 20 mM Tris-Cl (pH 8.0) containing 1 M NaCl. 50 μl supernatants from each collection tubes were tested for DC maturation effect. The collection tubes which showed DC maturation effect were selected, freeze dried, resuspended and dialyzed overnight with 20 mM Tris-Cl binding buffer at 4° C. (b) The active region was reloaded onto HiTrap CM FF and corrected the active regions as had done with Hitrap DEAE FF. (c) Active region was prepared at HiTrap CM FF reloaded onto HiTrap Blue HP and eluted with 50 mM KH2PO4 containing 1.5 M KCl (pH 7.0). Final active regions were analyzed for their protein contents by Mass spectrometry. ■ represents the protein concentration, ♦ activity to maturate the immature DC assessed with HLA-DR and CD86 monoclonal antibody using FACS analysis.

Example 6—Purification of Dendritic Cell Maturation Factors from CD4$^+$ iNKT Cells The supernatant of CD4$^+$ iNKT cells as described above were applied onto HiTrap DEAE FF column chromatography. Two (2) ml of Fast through and elutes were collected from each tube and 50 µl was used for testing DC maturation effect. Fifty (50) µl of eluate was added into a 96 well plate together with immature DC and the cells were cultured for 48 hours in 5% $CO_2$ incubator. The expression of HLA-DR and CD86 on DC were assessed by FACS analysis. The tubes that showed high expression level of HLA-DR and CD86 on surface of DC were labeled as active regions (FIG. 19a). The active regions were collected, freeze dried using freeze dryer, resuspended in 20 mM Tris-Cl (pH 8.0), and dialyzed at 4° C. overnight. The active regions were loaded onto HiTrap CM FF and separated and the protein contents were tested as done in anion chromatography. As seen in the results of cation chromatography, active regions were seen in both unbinding (No. 4-No. 11) and binding region (No. 27-No. 42) (FIG. 19b). The active regions from binding fractions were reloaded onto HiTrap Blue chromatography after dialysis of the protein samples in 50 mM $KH_2PO_4$. In case of Blue chromatography, the active regions were in binding region (No. 9-No. 17) (FIG. 19c). The active region was tested for protein contents using Mass spectrometry.

Example 7—S100A8 Showed DC Maturation Effect

Figure 12:
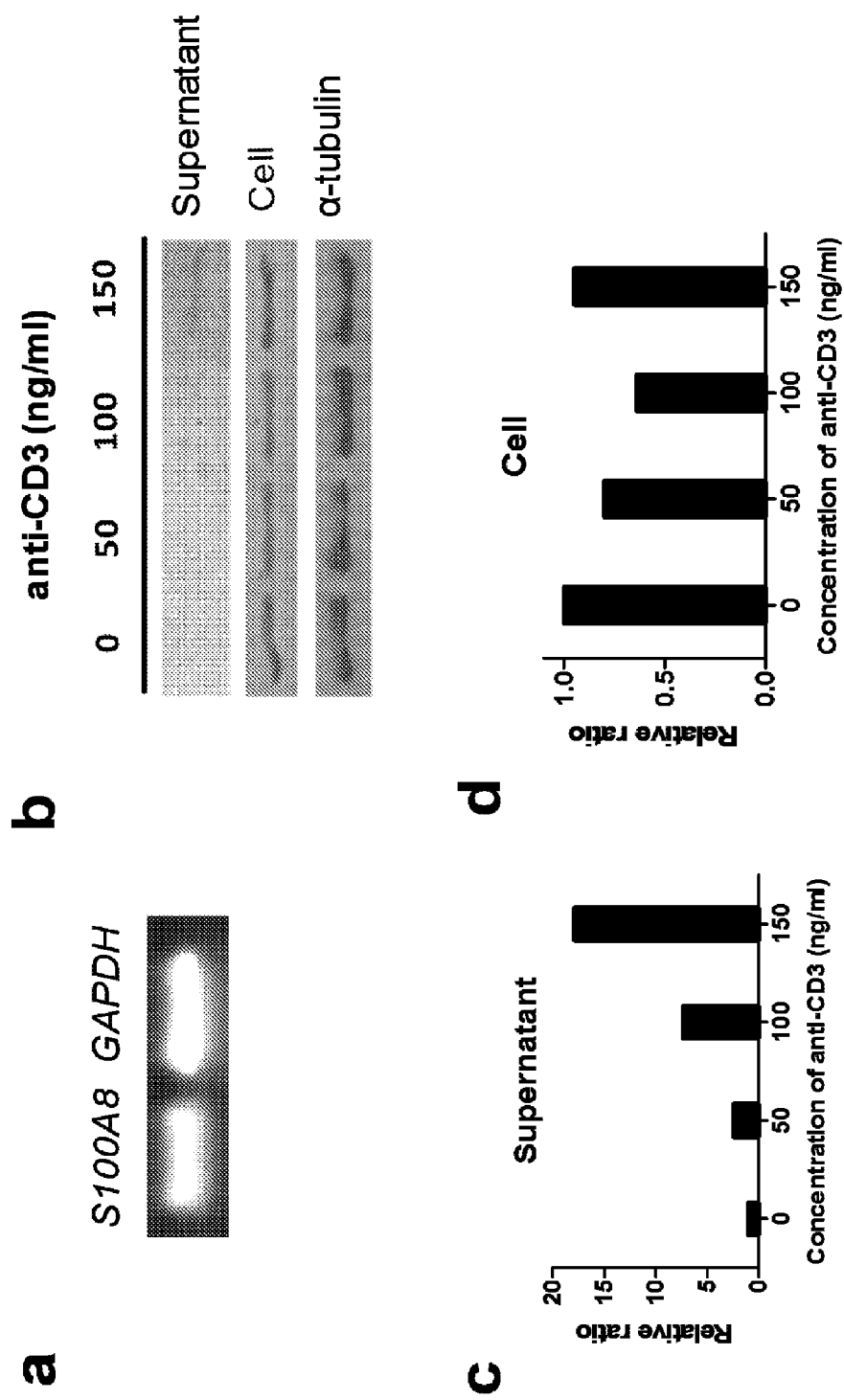
FIGS. 12A-D. Expression of S100A8 in CD4+iNKT cells and its culture supernatant. (a) RT-PCR, (b) Western blot, (c) relative expressed and secreted level of S100A8, (d) relative expression level of S100A8 in cells according to concentration of anti-CD3 antibody.
Figure 13:
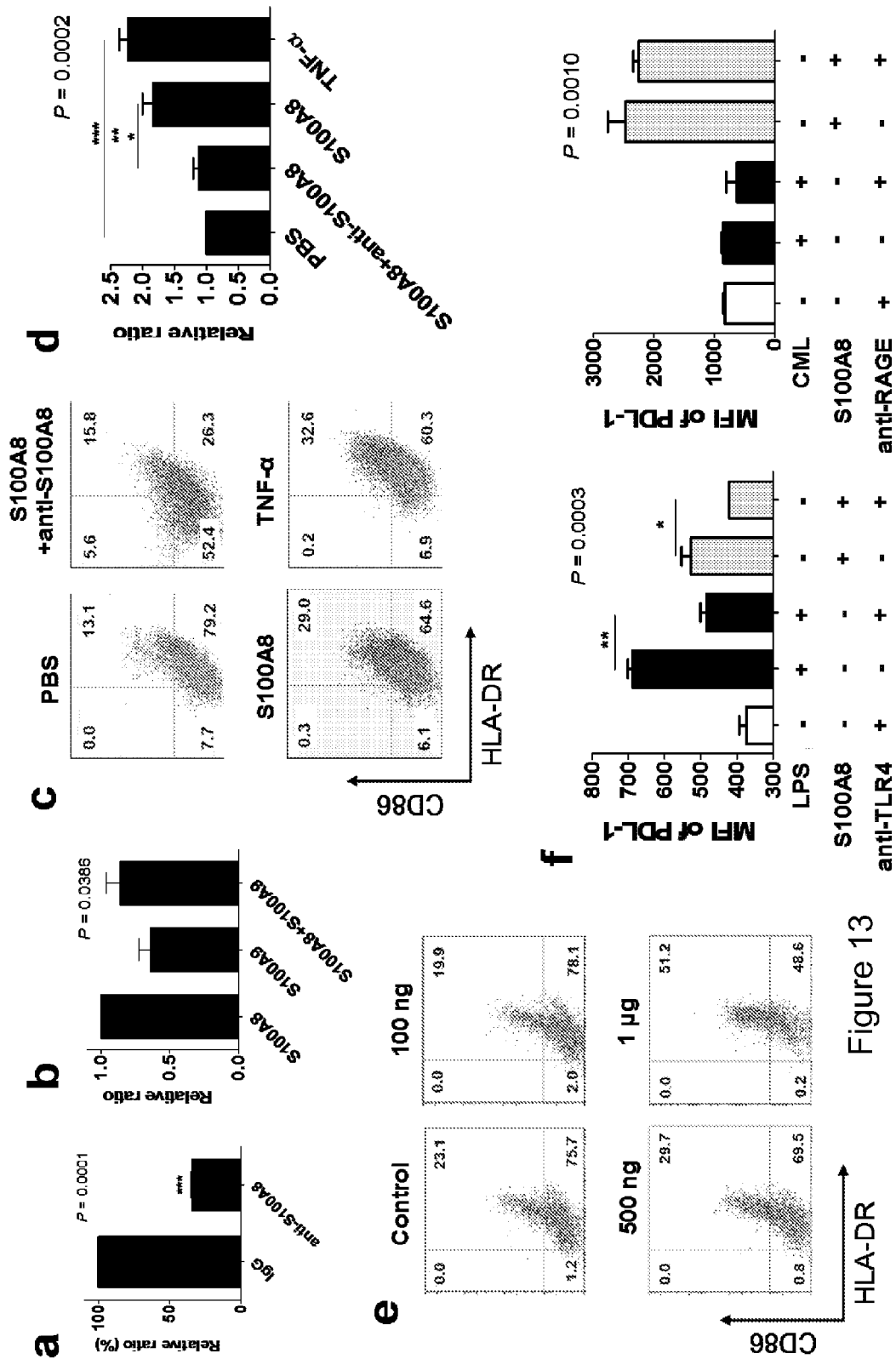
FIGS. 13A-F. Blocking effect of anti-S100A8 and anti-TLR4 on DC maturation. (a) 1 μg/ml anti-S100A8 antibody or IgG as control were pre-cultured with supernatant of CD4+ iNKT cells before adding immature DC. The maturation of immature DC was assessed by estimating the expression levels of CD86 and HLA-DR on the DC surface by FACS (t test, P=0.0001). (b) The effect of recombinant protein S100A8, S100A9, and S100A8-S100A9 complex on DC maturation (n=2). (c) Comparison of DC maturation effect of S100A8 and TNF-α. Immature DC were treated with PBS as control, 1 μg/ml S100A8, 1 μg/ml S100A8 and 1 μg/ml anti-S100A8 antibody, 100 ng/ml TNF-α. (d) Data showed relative ratio of various treatments. (e) Maturation effect of various concentration of S100A8 on immature DC. (f) PDL-1 expression in dendritic cells after stimulation with LPS, CML, and S100A8 with/without anti-TLR4 and/or anti-RAGE antibody. * $P<0.05$;  $P<0.001$; * $P<0.0001$. Results are representative of three independent experiments. Error bars indicate mean±s.d.
Figure 20:
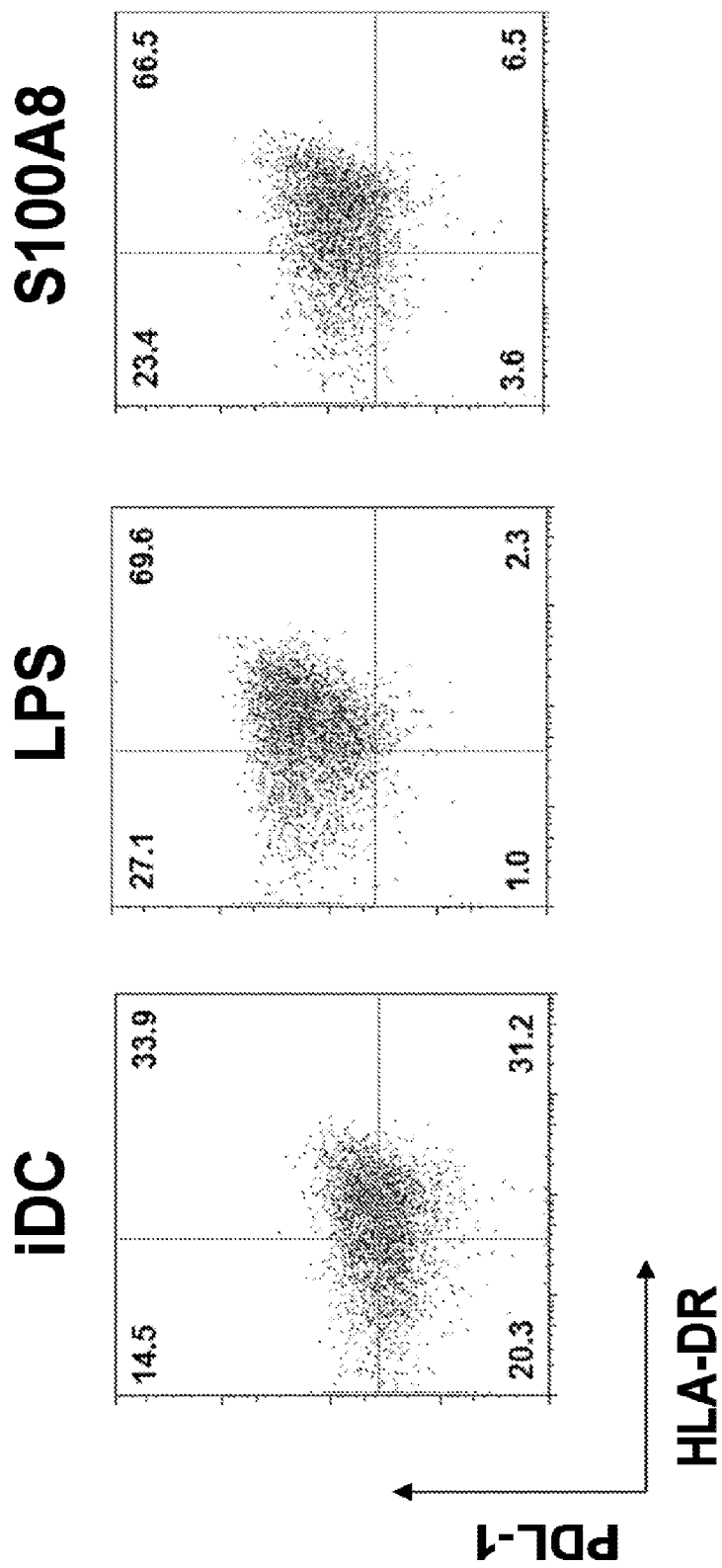
FIG. 20. Comparison of the effects of LPS and S100A8 on DC maturation. The maturation state of immature DC was assessed the expression level of PDL-1 and HLA-DR on the DC surface by FACS analysis.
Figure 21:
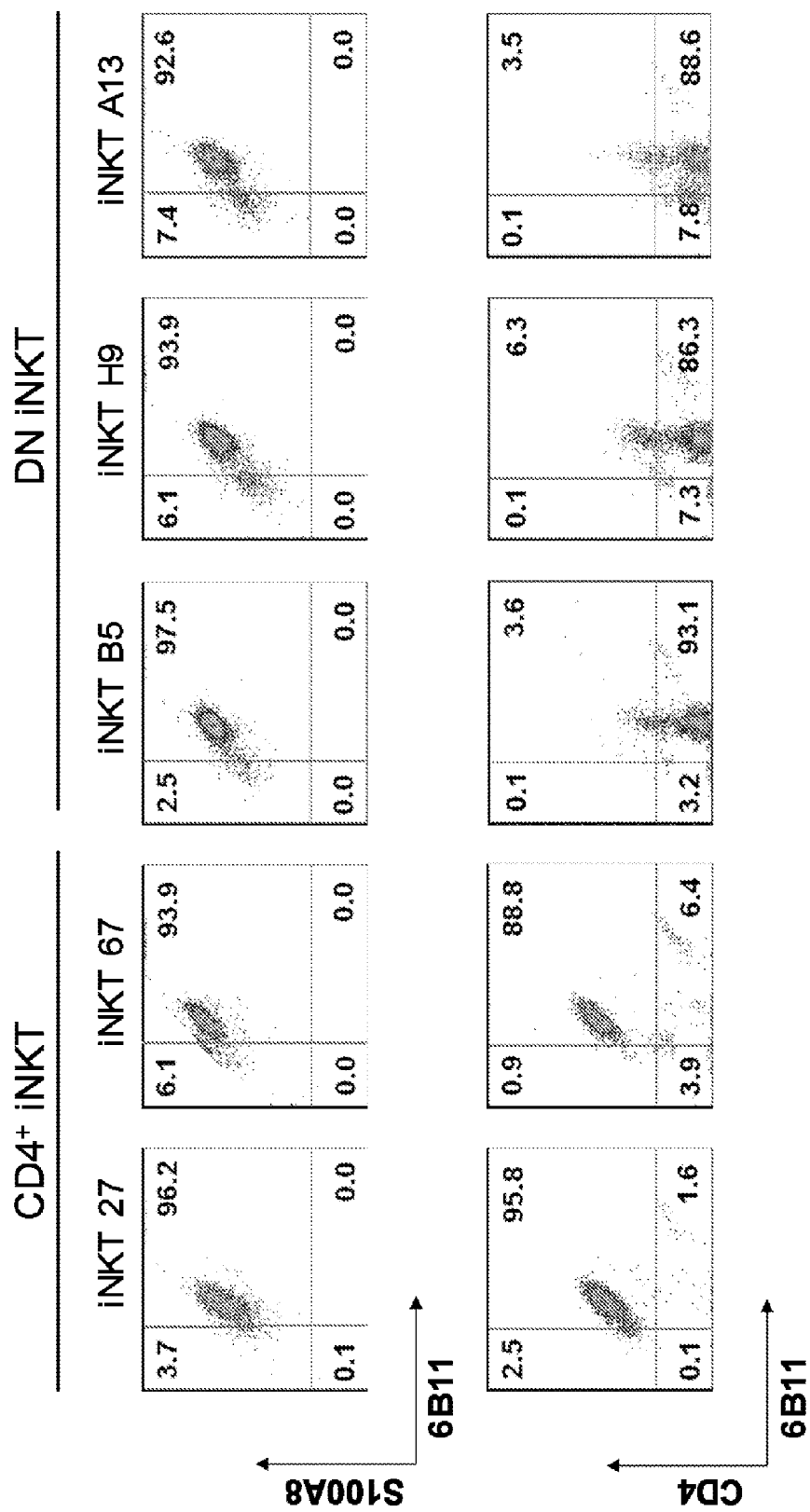
FIG. 21. Expression of S100A8 in CD4+ and DN iNKT cells. iNKT cells was stimulated with 100 ng/ml GalCer and γ-irradiated CD14+ APC for 7 days. iNKT cells confirmed by 6B11 antibody and CD4+ T cell by anti-CD4 antibody. The expression of S100A8 in iNKT cell subfamilies was confirmed by intracellular S100A8 staining.

Several interesting proteins were found in active regions of chromatography which showed DC maturation effect in 9 different experiments (sorted according to the number of hits from 9 independent purification series (Table 1)). Among them, S100A8 (S100 calcium-binding protein A8) hit 8 times, prolactin-induced protein (PIP) hit 7 times, ATP-binding cassette, desmoplakin isoform 1, haptoglobin, serpin peptidase inhibitor Glade A (member 3), transferrin, and transthyretin hit 6 times, ceruloplasmin, hemopexin, mesotrypsin, orosomucoid 1, and serine (or cystein) proteinase (clade B) hit 5 times. S100A9, counter partner of S100A8 hit 3 times and arginase I hit 3 times. Among these we tested iDC maturation effects of arginase I (R&D, Minneapolis, Minn.), mesotrypsin (rhTrypsin-3, R&D), S100A8 (Sino Biological, Beijing, China), S100A9 (Sino Biological), and PIP (OriGene, Rockville, Md.). We found that S100A8 and PIP showed of iDC maturation effect (FIG. 20). We confirmed the expression of S100A8 (FIG. 12a) in $CD4^+$ iNKT cells by RT-PCR. It was also verified both in supernatant and cell with western blot of S100A8 (FIGS. 13b, 13c, 13d, and 21). In the supernatants, the amount of S100A8 expression level was increased according to the concentration of anti-CD3 antibody (FIGS. 12b, 12c); however, such increase was not observed in cells (FIGS. 12b, 12d). To test the blocking effect of anti-S100A8 antibody on DC maturation, 1 µg/ml anti-S100A8 antibody or IgG as control was added with purified supernatant of $CD4^+$ iNKT cells to immature DC. The maturation of immature DC was assessed by checking the expression levels of CD86 and HLA-DR on the DC surface by FACS. Anti-S100A8 antibody (R&D) blocked the iDC maturation effect against supernatant of $CD4^+$ iNKT cell (P=0.0001, FIG. 13a). When we compared the effects of the individual subunits of the S100A8-S100A9 complex on DC maturation, we found that S100A8 alone and S100A8-S100A9 complex induced DC maturation. S100A9 did not induce the DC maturation compared to S100A8 alone (P=0.0386, FIG. 13b). We tested DC maturation effect of recombinant protein S100A8 and compared that of TNF-α. S100A8 induced the DC maturation like TNF-α. Additionally, anti-S100A8 antibody blocked the DC maturation effect of its S100A8 (FIGS. 13c, 13d). DC maturation effect by S100A8 was depended on its concentration (FIG. 13e).

Example 8—S100A8 Generates $T_{Reg}$ from Naïve T Cells Through Toll-Like Receptor 4

S100A8 binds the receptor for advanced glycation end products (RAGE) and toll like receptor 4 (TLR4) (Vogl et al., 2007; Boyd et al., 2008). Importantly, recombinant protein S100A8 recapitulates function, and both purified and recombinant induction of DC differentiation is blocked by anti-S100A8 and anti-TLR4 but not anti-RAGE mAbs. The combination of plate bound anti-MHC class II/CD1d antibody and/or S1000A8 induced DC differentiation that was qualitatively indistinguishable from co-culture of DC and iNKT cells or supplementation with supernatants from activated $CD4^+$ iNKT cells. S100A8 also induced $CD4^+CD25^+$ $Foxp3^+$ T cells ($T_{reg}$) from naïve T cells.

Figure 14:
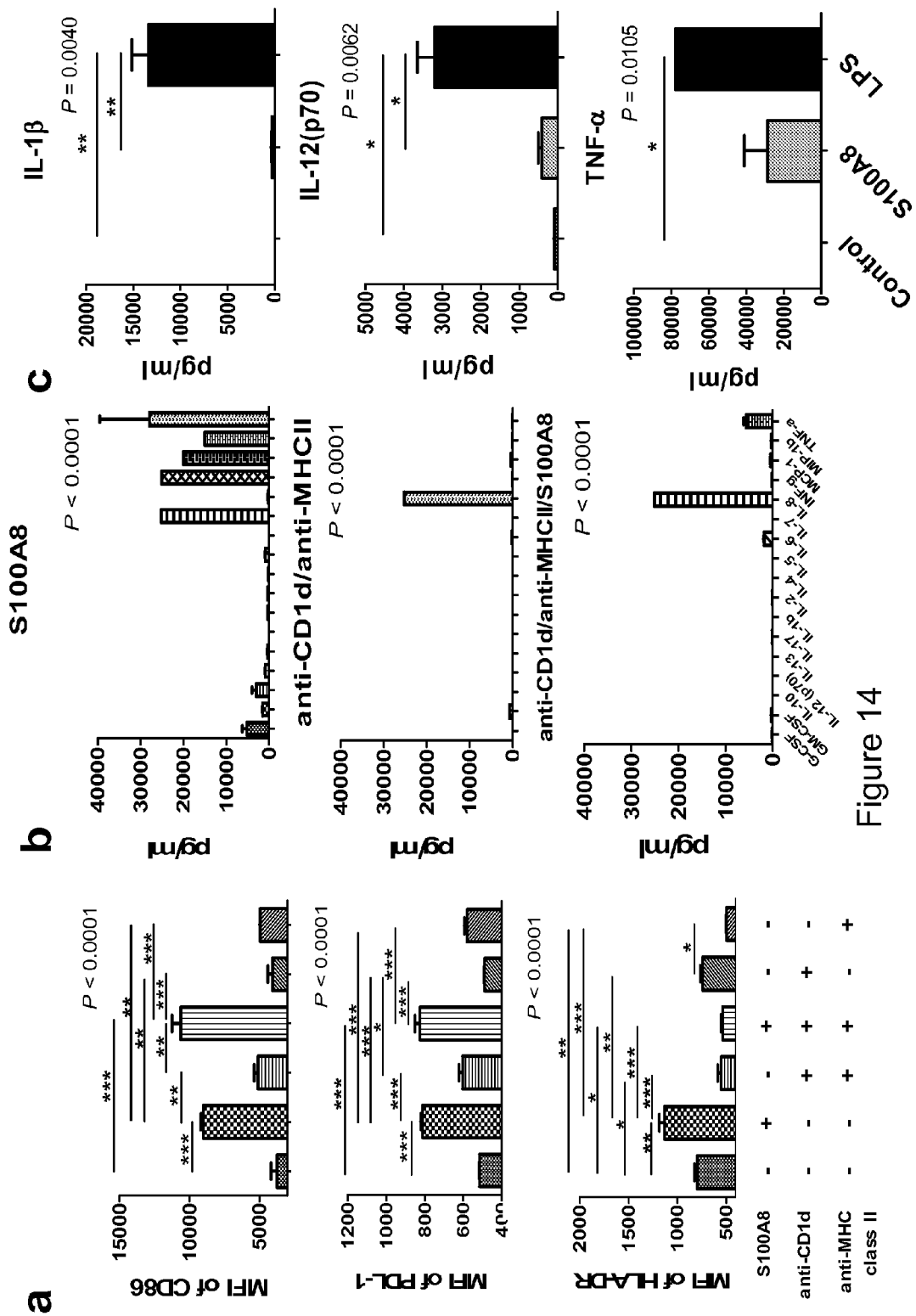
FIGS. 14A-C. Dendritic cell maturation by combination of S100A8, anti-CD1d antibody, and anti-MHC class II antibody. (a) Effect of combined plate-bound anti-CD1d/MHC class II antibody stimulation on DC maturation, (b) cytokine production, and (c) production of pro-inflammatory cytokines in S100A8 treated immature DC versus LPS treated immature DC. Immature DC transferred to anti-CD1d/MHC class II antibody coated plate, and cultured for 48 hours with or without soluble S100A8 to allow the induction of tolerogenic DC. Cytokines were analyzed by Bio-Plex pro human cytokine 17-plex assay kit (Bio-Rad). * $P<0.05$; ** $P<0.001$. Error bars indicate mean±s.d.
Figure 22:
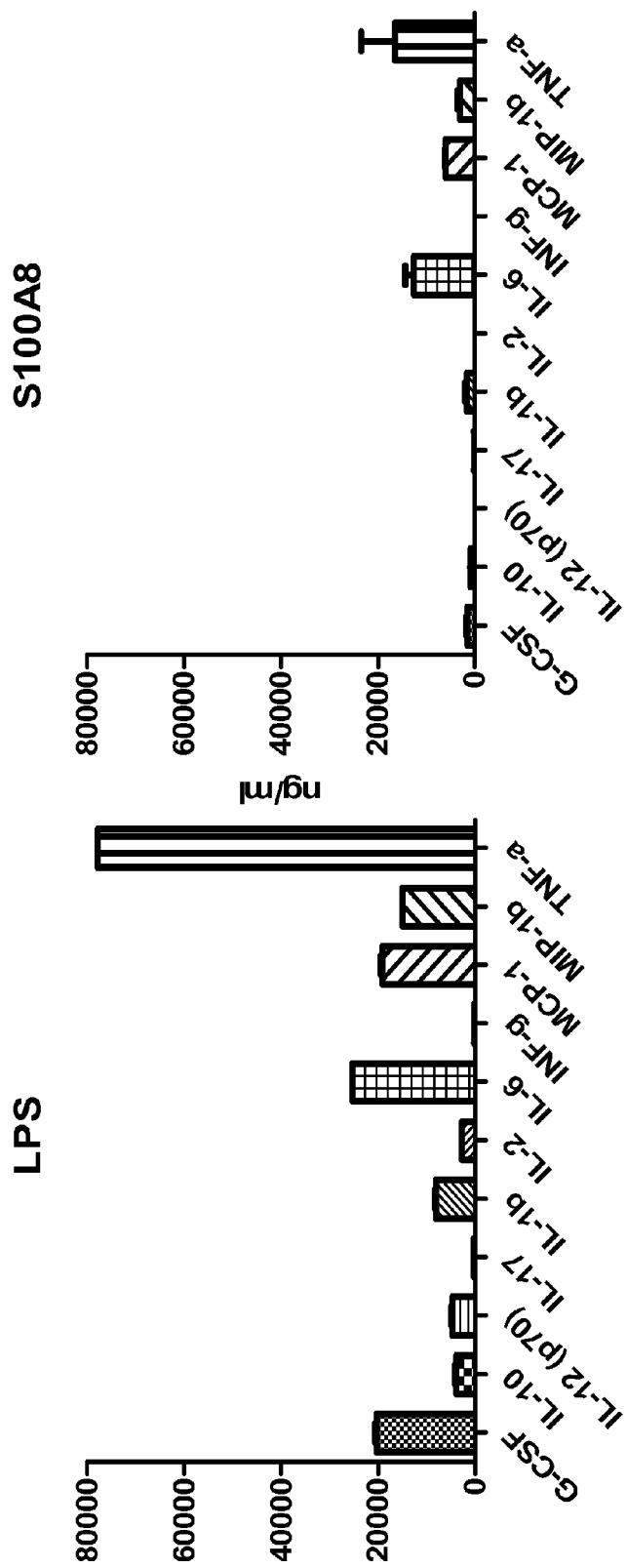
FIG. 22. Cytokine production profiles of matured DC induced by LPS and S100A8. Cytokines in the supernatants obtained from matured DC upon treatments with 1 μg/ml LPS or 1 μg/ml S100A8 for 48 hours were analyzed by using Bio-Plex pro human cytokine 17-plex assay kit (Bio-Rad).
Figure 23:
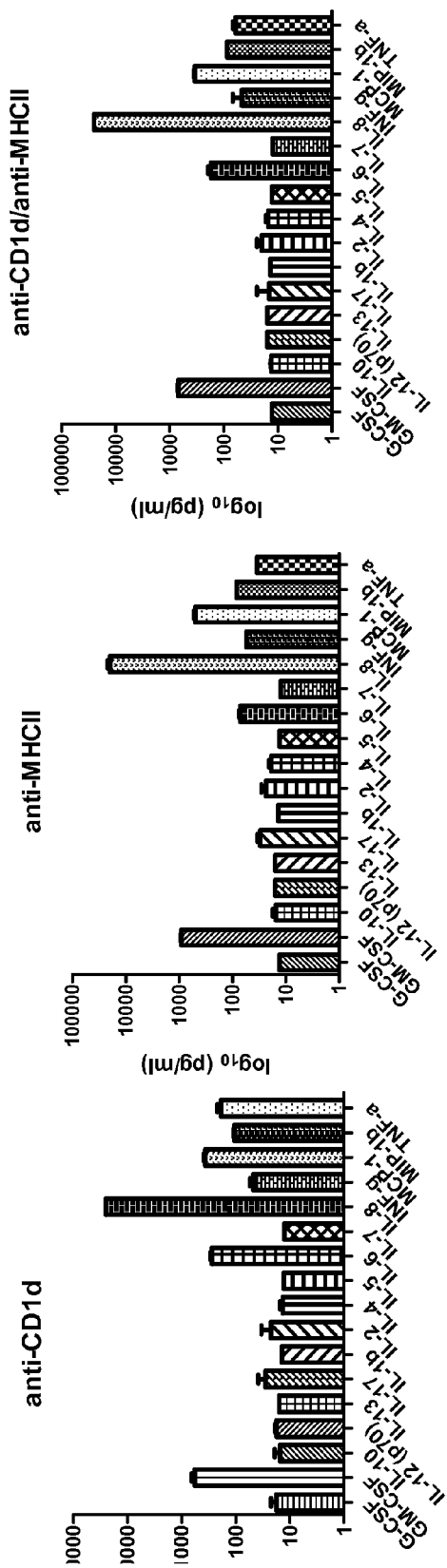
FIG. 23. Cytokine production profiles of mature DC induced by anti-CD1d and anti-MHC class II antibodies. Cytokines in the supernatants obtained from mature DC upon treatments with 1 μg/ml anti-CD1d and/or 1 μg/ml anti-MHC class II antibodies for 48 hours were analyzed by using Bio-Plex pro human cytokine 17-plex assay kit (Bio-Rad).
Figure 24:
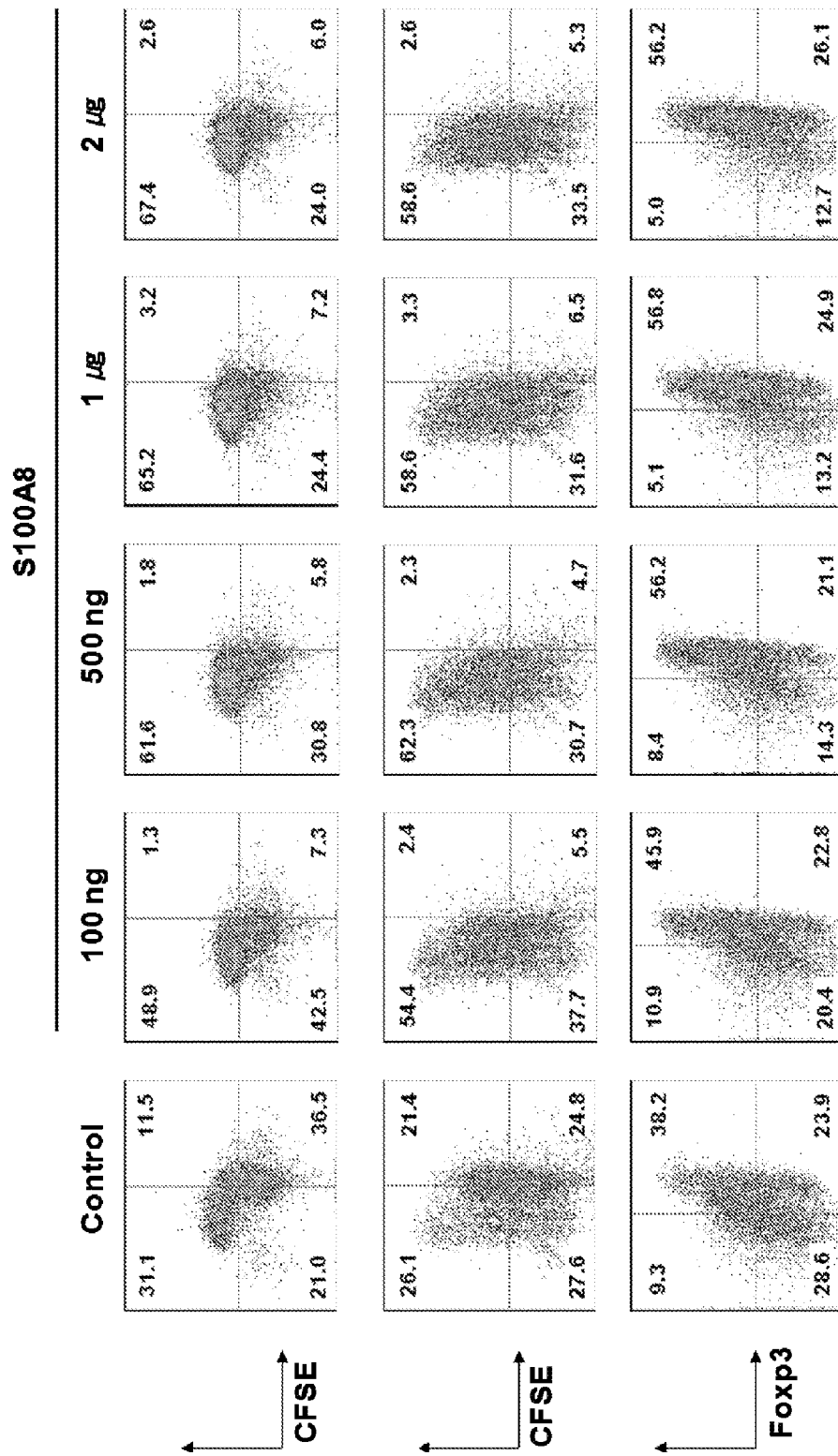
FIG. 24. $T_{reg}$ generation at various concentrations of S100A8. Tolerogenic DC were induced by various concentrations of S100A8. CFSE labeled CD4+CD25-Foxp3- T cells were added to tolerogenic DC to evaluate the $T_{reg}$ generation by FACS analysis.
Figure 25:
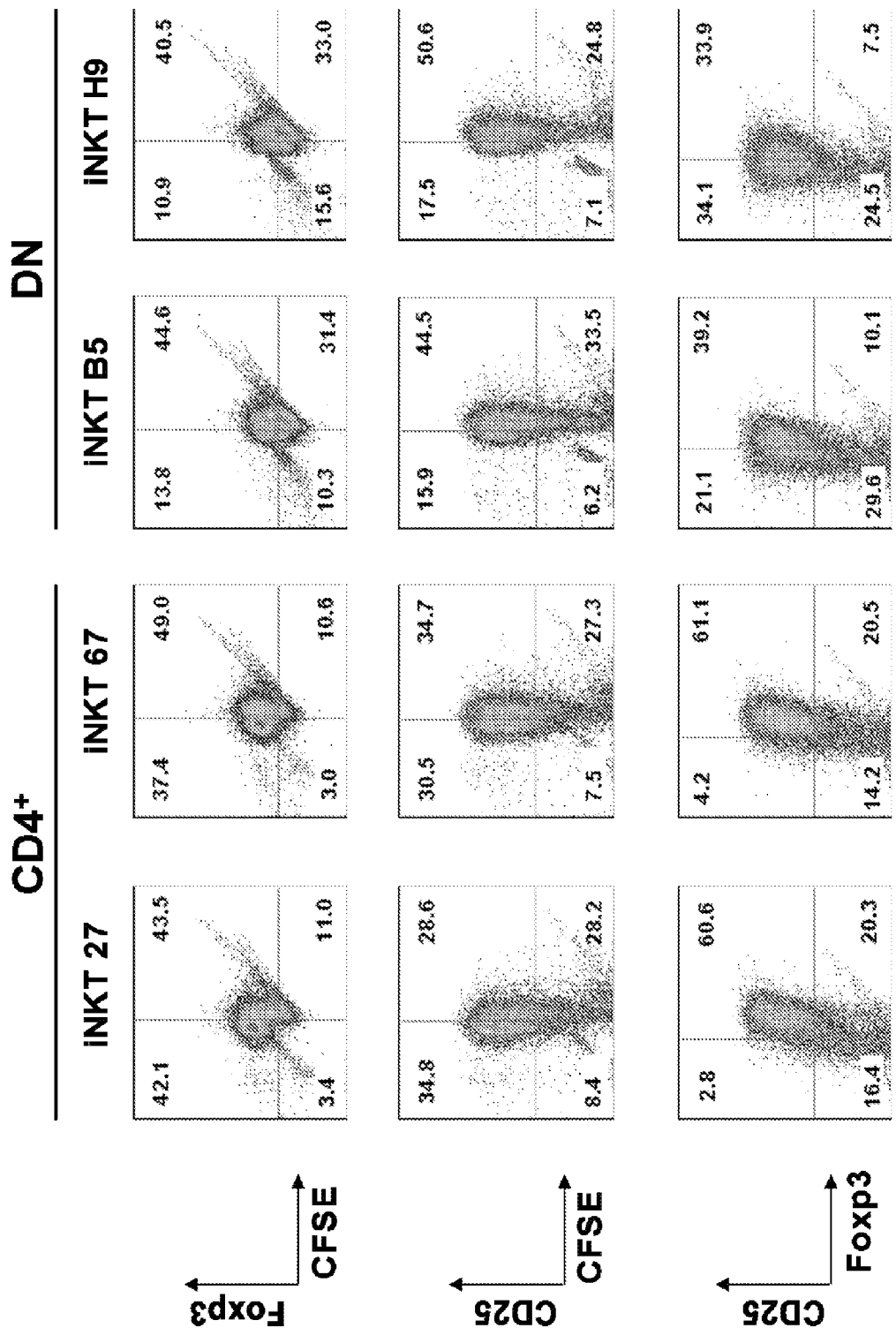
FIG. 25. Comparison between the $T_{reg}$ generation by supernatants of CD4+ iNKT and DN iNKT cells. Supernatants were obtained from pre-coated 200 ng/ml of anti-CD3 antibody treated iNKT cells. Supernatants were added into immature DC for inducing DC maturation. CFSE labeled CD4+CD25−Foxp3− T cells were added to tolerogenic DC by supernatants of iNKT cells to evaluate the $T_{reg}$ generation by FACS analysis.

DC maturation by S100A8 was blocked by adding anti-TLR4 antibody. $N^\epsilon$-carboxymethyllysine (CML), agonist of RAGE, did not induce the DC maturation and did not inhibit the maturation effect of S100A8 (FIG. 13f). It means that S100A8 induction of DC maturation might be transmitted via TLR4 signaling. Increase in CD86 and PDL-1 expression on DC surface by anti-CD1d/MHC class II antibody and S100A8 combination was higher than any other combination or single application on immature DC, but such effect was not observed on HLA-DR expression on DC surface (FIG. 14a). Several cytokines were secreted by S100A8 treated DC, including G-CSF, GM-CSF, IFN-γ, IL-10, IL-6, IL-8, MCP-1, MIP-1b, and TNF-α (FIGS. 14b and 22). But combination of anti-CD1d and anti-MHC class II antibody induced IL-8 (FIGS. 14b and 23). Except IL-8, most of cytokines which were induced by S100A8, were reduced or blocked by treatment together with anti-CD1d and anti-MHC class II antibody (FIG. 14b). TLR activation with LPS was reported to be an on/off signal that decides proinflammatory or tolerogenic DC maturation after interaction with iNKT cells (Caielli et al., 2010). Importantly, we found that S100A8 activates DC through TLR4 and unidentified receptors. When compared to LPS, S100A8 induces IL-10, G-CSF, and PDL-1 and significantly much less amount of IL-1β, IL-12, TNF-α (FIG. 14c), and IL-6 (FIG. 23) (Chen et al., 2004). Comparing the ability in $T_{reg}$ generation between these combinations, S100A8 treated DC group and anti-CD1d antibody, anti-MHC class II antibody, and S100A8 treated DC group generated $T_{reg}$ cells significantly, but not in anti-CD1d and anti-MHC class II antibody treated groups (P=0.0050, FIGS. 15a, 15b). Additionally, $T_{reg}$ cell generation was increased and dependent on the concentration of S100A8 (FIG. 24).

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Porcelli, S. et al. Analysis of T cell antigen receptor (TCR) expression by human peripheral blood CD4-8-alpha/beta T cells demonstrates preferential use of several V beta genes and an invariant TCR alpha chain. *J. Exp. Med.* 178, 1-16 (1993).

Naidenko, O. V. et al. Binding and antigen presentation of ceramide-containing glycolipids by soluble mouse and human CD1d molecules. *J. Exp. Med.* 190, 1069-1080 (1999).

Wilson, S. B. et al. Multiple differences in gene expression in regulatory Vα24JαQ T cells from identical twins discordant for type I diabetes. *Proc. Natl. Acad. Sci. U.S.A* 97, 7411-7416 (2000).

Moodycliffe, A. M., Nghiem, D., Clydesdale, G. & Ullrich, S. E. Immune suppression and skin cancer development: regulation by NKT cells. *Nat. Immunol.* 1, 521-525 (2000).

Naumov, Y. N. et al. Activation of CD1d-restricted T cells protects NOD mice from developing diabetes by regulating dendritic cell subsets. *Proc. Natl. Acad. Sci. U.S.A.* 98, 13838-13843 (2001).

Sharif, S. et al. Activation of natural killer T cells by α-galactosylceramide treatment prevents the onset and recurrence of autoimmune Type 1 diabetes. *Nat. Med.* 7, 1057-1062 (2001).

Wilson, S. B. et al. Extreme Th1 bias of invariant Valpha24JalphaQ T cells in type 1 diabetes. *Nature* 391, 177-181 (1998).

Behar, S. M., Dascher, C. C., Grusby, M. J., Wang, C. R. & Brenner, M. B. Susceptibility of Mice deficient in CD1d or TAP1 to infection with *Mycobacterium tuberculosis*. *J. Exp. Med.* 189, 1973-1980 (1999).

Kakimi, K., Guidotti, L. G., Koezuka, Y. & Chisari, F. V. Natural killer T cell activation inhibits Hepatitis B Virus replication in vivo. *J. Exp. Med.* 192, 921-930 (2000).

Gonzalez-Aseguinolaza, G. et al. α-Galactosylceramide-activated Vα14 natural killer T cells mediate protection against murine malaria. *Proc. Natl. Acad. Sci. U.S.A* 97, 8461-8466 (2000).

Hegde, S. et al. NKT cells direct monocytes into a DC differentiation pathway. *J. Leuko. Biol.* 81, 1224-1235 (2007).

Hori, S., Nomura, T. & Sakaguchi, S. Control of regulatory T cell development by the transcription factor Foxp3. *Science* 299, 1057-1061 (2003).

Vogl, T. et al. Mrp8 and Mrp14 are endogenous activators of Toll-like receptor 4, promoting lethal, endotoxin-induced shock. *Nat. Med.* 13, 1042-1049 (2007).

Exley, M. A. et al. Selective activation, expansion, and monitoring of human iNKT cells with a monoclonal antibody specific for the TCR α-chain CDR3 loop. *Eur. J. Immunol.* 38, 1756-1766 (2008).

Hou, R., Goloubeva, O., Neuberg, D. S., Strominger, J. L. & Wilson, S. B. Interleukin-12 and interleukin-2-induced invariant natural killer T-cell cytokine secretion and perforin expression independent of T-cell receptor activation. *Immunol.* 110, 30-37 (2003).

Ferret-Bernard, S., Curwen, R. S. & Mountford, A. P. Proteomic profiling reveals that Th2 inducing dendritic cells stimulated with helminth antigens have a 'limited maturation' phenotype. *Proteomics* 8, 980-993 (2008).

Vincent, M. S. et al. CD1-dependent dendritic cell instruction. *Nat. Immunol.* 3, 1163-1168 (2002).

Wilson, S. B. & Delovitch, T. L. Janus-like role of regulatory iNKT cells in autoimmune disease and tumor immunity. *Nat. Rev. Immunol.* 3, 211-222 (2003).

Hegde, S., Fox, L., Wang, X. & Gumperz, J. E. Autoreactive natural killer T cells: promoting immune protection and immune tolerance through varied interactions with myeloid antigen-presenting cells. *Immunol.* 130, 471-483 (2010).

Mars, L. T. et al. Invariant NKT cells inhibit development of the Th17 lineage. *Immunol.* 106, 6238-6243 (2009).

Hayflick, J. S., Kilgannon, P., & Gallatin, W. M. The intercellular adhesion molecule (ICAM) family of proteins. *Immunol. Res.* 17, 313-327 (1998).

Takahashi, T. et al. Analysis of human V alpha 24+ CD4+ NKT cells activated by alpha-glucosylceramide-pulsed monocyte-derived dendritic cells. *J. Immunol.* 164, 4458-4464 (2000).

Boyd, J. H. et al. S100A8 and S100A9 mediate endotoxin-induced cardiomyocyte dysfunction via the receptor for advanced glycation end products. *Circ. Res.* 102, 1239-1246 (2008).

Caielli, S. et al. On/off TLR signaling decides proinflammatory of tolerogenic dendritic cell maturation upon CD1d-mediated interaction with invariant NKT cells. *J. Immunol.* 185, 7317-7329 (2010).

Chen, X. et al. Phosphatidylserine regulates the maturation of human dendritic cells. *J. Immunol.* 13, 2985-2994 (2004).

Hermans, I. F. et al. Dendritic cell function can be modulated through cooperative actions of TLR ligands and invariant NKT cells. *J. Immunol.* 178, 2721-2729 (2007).

Steinman, R. M. & Nussenzweig, M. C. Inaugural Article: Avoiding horror autotoxicus: The importance of dendritic cells in peripheral T cell tolerance. *Proc. Natl. Acad. Sci. U.S.A.* 99, 351-358 (2002).

Jonuleit, H., Schmitt, E., Schuler, G., Knop, J. & Enk, A. H. Induction of interleukin 10-producing, nonproliferating CD4(+) T cells with regulatory properties by repetitive stimulation with allogeneic immature human dendritic cells. *J. Exp. Med.* 192, 1213-1222 (2000).

Albert, M. L., Jegathesan, M. & Darnell, R. B. Dendritic cell maturation is required for the cross-tolerization of CD8+ T cells. *Nat. Immunol.* 2, 1010-1017 (2001).

Tang, Q. et al. Visualizing regulatory T cell control of autoimmune responses in nonobese diabetic mice. *Nat. Immunol.* 7, 83-92 (2006).

Banchereau, J. et al. Immunobiology of dendritic cells. *Annu. Rev. Immunol.* 18, 767-811 (2000).

Rissoan, M. C. Reciprocal control of T helper cell and dendritic cell differentiation. *Science* 283, 1183-1186 (1999).

Liu, Y. J., Kanzler, H., Soumelis, V. & Gilliet, M. Dendritic cell lineage, plasticity and cross-regulation. *Nat. Immunol.* 2, 585-589 (2001).

Kitamura, H. et al. The natural killer T (NKT) cell ligand alpha-galactosylceramide demonstrates its immunopotentiating effect by inducing interleukin (IL)-12 production by dendritic cells and IL-12 receptor expression on iNKT cells. *J. Exp. Med.* 189, 1121-1128 (1999).

Contasta, I. et al. Relationships between the activity of MMP1/TIMP1 enzymes and the Th1/Th2 cytokine network. *Cancer Biother. Radiopharm.* 14, 465-475 (1999).

We claim:

1. A method for producing regulatory T cells comprising: contacting immature dendritic cells with a composition comprising prolactin induced protein (PIP) or S100 calcium binding protein A8 (S100A8) or a combination of PIP and S100A8 to produce tolerogenic dendritic cells, and
contacting naïve T-cells with said tolerogenic DCs to produce regulatory T (Treg) cells.

2. The method of claim 1, wherein said composition comprises mature PIP or PIP comprising a leader sequence.

3. The method of claim 2, wherein said PIP comprises SEQ ID NO: 2 or SEQ ID NO: 3.

4. The method of claim 1, wherein said composition comprises S100A8.

5. The method of claim 4, wherein said S100A8 comprises SEQ ID NO: 1.

6. The method of claim 1, wherein said composition comprises a combination of PIP and S100A8.

7. The method of claim 1 wherein the regulatory T cell is CD4$^+$CD25$^+$Foxp3$^+$.

8. A method of treating an autoimmune disease in a subject, said method comprising:
(a) obtaining a population of subject-compatible naïve T cells;
(b) contacting immature dendritic cells with a composition comprising prolactin induced protein (PIP) or S100 calcium binding protein A8 (S100A8) or a combination of PIP and S100A8 to produce a population of tolerogenic dendritic cells;
(c) contacting said population of subject-compatible naïve T cells with said population of tolerogenic dendritic cells to produce a population of $T_{reg}$ cells; and
(d) introducing said population of $T_{reg}$ cells into said subject to treat said autoimmune disease.

9. The method of claim 8, wherein the population of naïve T-cells cells is obtained from said subject or obtained from a donor distinct from said subject.

10. The method of claim 8, wherein said method further comprises expanding the population of $T_{reg}$ cells produced in step (c) and/or isolating $T_{reg}$ cells from the expanded population of $T_{reg}$ cells or from the population of $T_{reg}$ cells obtained in step (c).

11. The method of claim 8, wherein said autoimmune or inflammatory disease is selected from Addison's disease, autoimmune hepatitis, autoimmune hyperlipidemia, autoimmune myocarditis, autoimmune pancreatitis, autoimmune retinopathy, axonal and neuronal neuropathies, cardiomyopathy, Crohn's disease, Insulin dependent Diabetes (Type 1 diabetes), juvenile diabetes, multiple sclerosis (MS), systemic lupus erythematosus (SLE), Lyme disease, palindromic rheumatism, psoriasis, psoriatic arthritis, rheumatic fever, and rheumatoid arthritis.

\* \* \* \* \*

SEQUENCE LISTING

<160> NUMBER OF SEQ ID NOS: 5

<210> SEQ ID NO 1
<211> LENGTH: 93
<212> TYPE: PRT
<213> ORGANISM: Homo sapiens

<400> SEQUENCE: 1

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 2
<211> LENGTH: 146
<212> TYPE: PRT
<213> ORGANISM: Homo sapiens

<400> SEQUENCE: 2

Met Arg Leu Leu Gln Leu Leu Phe Arg Ala Ser Pro Ala Thr Leu Leu
1               5                   10                  15

Leu Val Leu Cys Leu Gln Leu Gly Ala Asn Lys Ala Gln Asp Asn Thr
            20                  25                  30

Arg Lys Ile Ile Ile Lys Asn Phe Asp Ile Pro Lys Ser Val Arg Pro
        35                  40                  45

Asn Asp Glu Val Thr Ala Val Leu Ala Val Gln Thr Glu Leu Lys Glu
    50                  55                  60

Cys Met Val Val Lys Thr Tyr Leu Ile Ser Ser Ile Pro Leu Gln Gly
65                  70                  75                  80

Ala Phe Asn Tyr Lys Tyr Thr Ala Cys Leu Cys Asp Asp Asn Pro Lys
                85                  90                  95

Thr Phe Tyr Trp Asp Phe Tyr Thr Asn Arg Thr Val Gln Ile Ala Ala
            100                 105                 110

Val Val Asp Val Ile Arg Glu Leu Gly Ile Cys Pro Asp Asp Ala Ala
        115                 120                 125

Val Ile Pro Ile Lys Asn Asn Arg Phe Tyr Thr Ile Glu Ile Leu Lys
    130                 135                 140

Val Glu
145

<210> SEQ ID NO 3
<211> LENGTH: 118
<212> TYPE: PRT
<213> ORGANISM: Homo sapiens

<400> SEQUENCE: 3

Gln Asp Asn Thr Arg Lys Ile Ile Ile Lys Asn Phe Asp Ile Pro Lys
1               5                   10                  15

Ser Val Arg Pro Asn Asp Glu Val Thr Ala Val Leu Ala Val Gln Thr
            20                  25                  30

-continued

```
Glu Leu Lys Glu Cys Met Val Val Lys Thr Tyr Leu Ile Ser Ser Ile
         35              40              45

Pro Leu Gln Gly Ala Phe Asn Tyr Lys Tyr Thr Ala Cys Leu Cys Asp
     50              55              60

Asp Asn Pro Lys Thr Phe Tyr Trp Asp Phe Tyr Thr Asn Arg Thr Val
 65              70              75              80

Gln Ile Ala Ala Val Val Asp Val Ile Arg Glu Leu Gly Ile Cys Pro
             85              90              95

Asp Asp Ala Ala Val Ile Pro Ile Lys Asn Asn Arg Phe Tyr Thr Ile
            100             105             110

Glu Ile Leu Lys Val Glu
        115

<210> SEQ ID NO 4
<211> LENGTH: 27
<212> TYPE: DNA
<213> ORGANISM: Artificial sequence
<220> FEATURE:
<223> OTHER INFORMATION: S100A8-F sense sequence

<400> SEQUENCE: 4
accgagctgg agaaagcctt gaactct                                   27

<210> SEQ ID NO 5
<211> LENGTH: 27
<212> TYPE: DNA
<213> ORGANISM: Artificial sequence
<220> FEATURE:
<223> OTHER INFORMATION: S100A8-R antisense sequence

<400> SEQUENCE: 5
ctctttgtgg ctttcttcat ggctttt                                   27
```